(12) United States Patent
Keitel

(10) Patent No.: US 11,033,685 B2
(45) Date of Patent: Jun. 15, 2021

(54) INJECTION DEVICE

(71) Applicant: Haselmeier AG, St. Gallen (CH)

(72) Inventor: Joachim Keitel, Esslingen (DE)

(73) Assignee: HASELMEIER AG, St. Gallen (CH)

(*) Notice: Subject to any disclaimer, the term of this patent is extended or adjusted under 35 U.S.C. 154(b) by 588 days.

(21) Appl. No.: 15/960,104

(22) Filed: Apr. 23, 2018

(65) Prior Publication Data

US 2018/0236171 A1    Aug. 23, 2018

Related U.S. Application Data

(63) Continuation of application No. PCT/EP2016/001696, filed on Oct. 12, 2016.

(30) Foreign Application Priority Data

Oct. 22, 2015   (DE) .................... 20 2015 007 351.4

(51) Int. Cl.
*A61M 5/20* (2006.01)
*A61M 5/315* (2006.01)
*A61M 5/32* (2006.01)

(52) U.S. Cl.
CPC ...... *A61M 5/2033* (2013.01); *A61M 5/31528* (2013.01); *A61M 5/31551* (2013.01); *A61M 5/31563* (2013.01); *A61M 5/31583* (2013.01); *A61M 5/3202* (2013.01); *A61M 5/3204* (2013.01)

(58) Field of Classification Search
CPC .................. A61M 5/2033; A61M 5/31563
See application file for complete search history.

(56) References Cited

U.S. PATENT DOCUMENTS

| 4,194,505 A | * | 3/1980 | Schmitz ............. A61M 5/2033 604/138 |
| 6,241,709 B1 | | 6/2001 | Bechtold et al. |
| 9,308,327 B2 | | 4/2016 | Marshall et al. |

(Continued)

FOREIGN PATENT DOCUMENTS

| WO | 2010115670 A1 | 10/2010 | |
| WO | 2013117332 A1 | 8/2013 | |
| WO | WO-2014121929 A1 * | 8/2014 | ........ A61M 5/31551 |

OTHER PUBLICATIONS

International search report dated Feb. 10, 2017 for international application PCT/EP2016/001696 on which this application is based.

*Primary Examiner* — Jenna Zhang
(74) *Attorney, Agent, or Firm* — Global IP Counselors, LLP

(57) ABSTRACT

An injection device is for automatically squeezing injection liquid from a container and includes: a housing; an injection spring configured to cause squeezing of the injection liquid from the container; the injection device defining a longitudinal central axis and a proximal direction; a metering piston mounted so as to be movable in the direction of the longitudinal central axis of the injection device; the metering piston being configured to, when squeezing injection liquid, move in the proximal direction; a setting device for setting the quantity of injection liquid to be squeezed; an end stop which establishes a terminal position of the metering piston; and, the setting device having an adjustment unit configured to adjust the position of the end stop.

12 Claims, 17 Drawing Sheets

(56) References Cited

U.S. PATENT DOCUMENTS

| | | | |
|---|---|---|---|
| 9,849,243 B2 | 12/2017 | Marshall et al. | |
| 2001/0034507 A1* | 10/2001 | Kirchhofer | A61M 5/31553 604/211 |
| 2002/0016571 A1* | 2/2002 | Kirchhofer | A61M 5/31563 604/218 |
| 2002/0165500 A1* | 11/2002 | Bechtold | A61M 5/31553 604/209 |
| 2008/0183139 A1* | 7/2008 | Burren | A61M 5/31585 604/211 |
| 2009/0240195 A1* | 9/2009 | Schrul | A61M 5/31553 604/71 |
| 2010/0010454 A1* | 1/2010 | Marshall | A61M 5/2033 604/208 |
| 2012/0029443 A1* | 2/2012 | Holmqvist | A61M 5/20 604/211 |

* cited by examiner

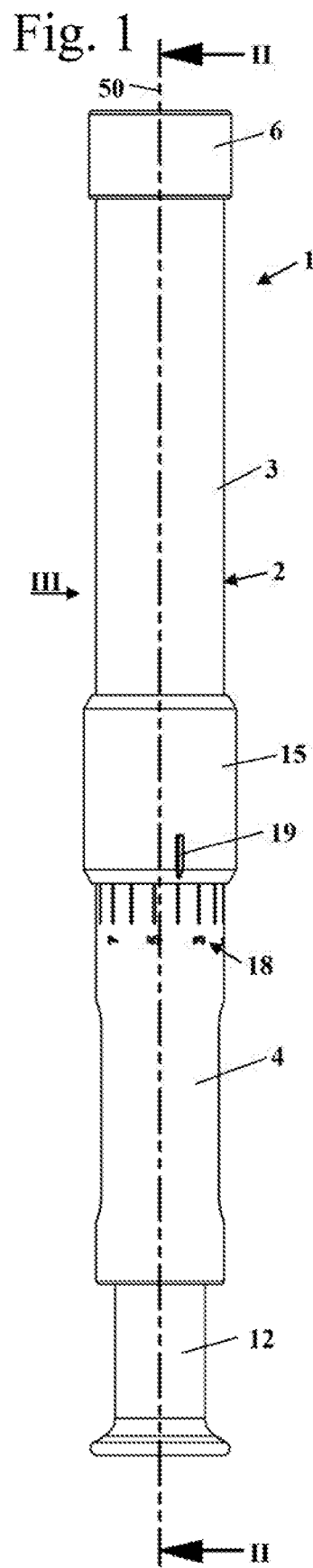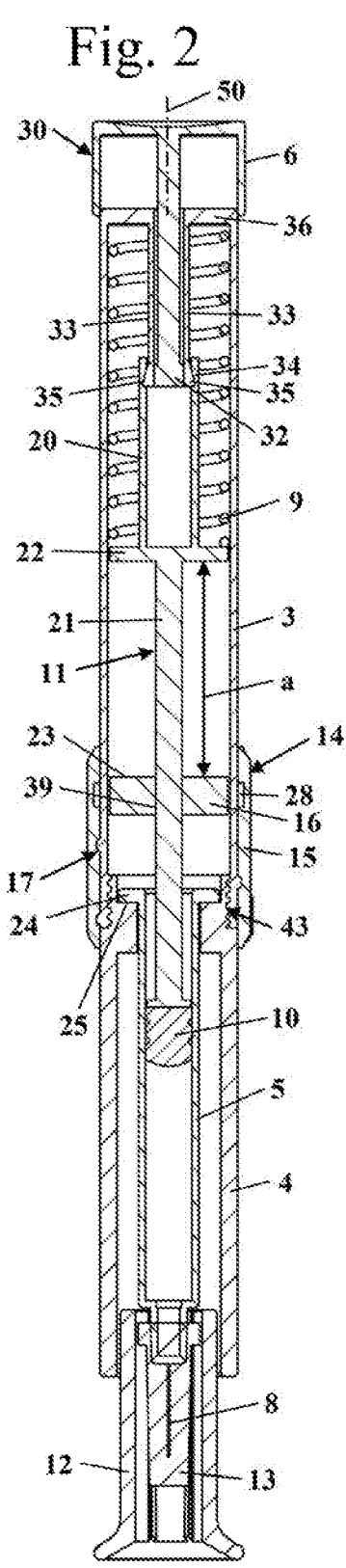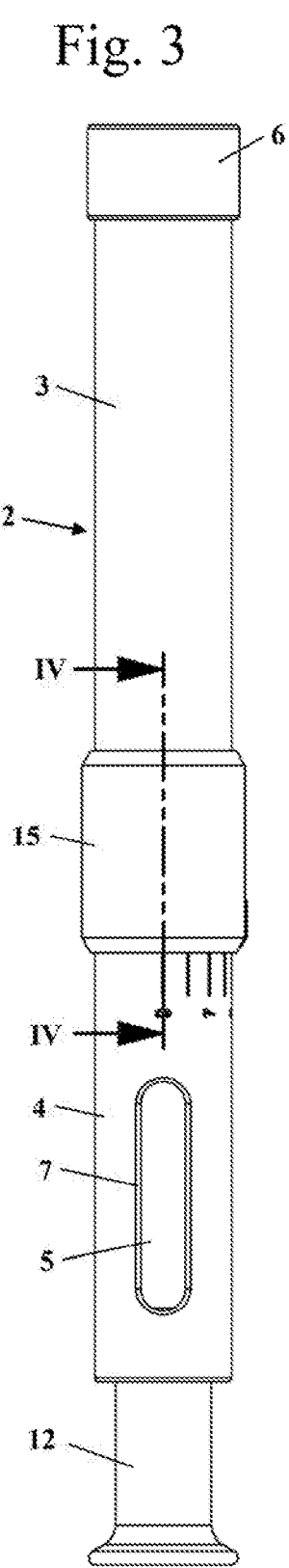

Fig. 7
Fig. 8
Fig. 9
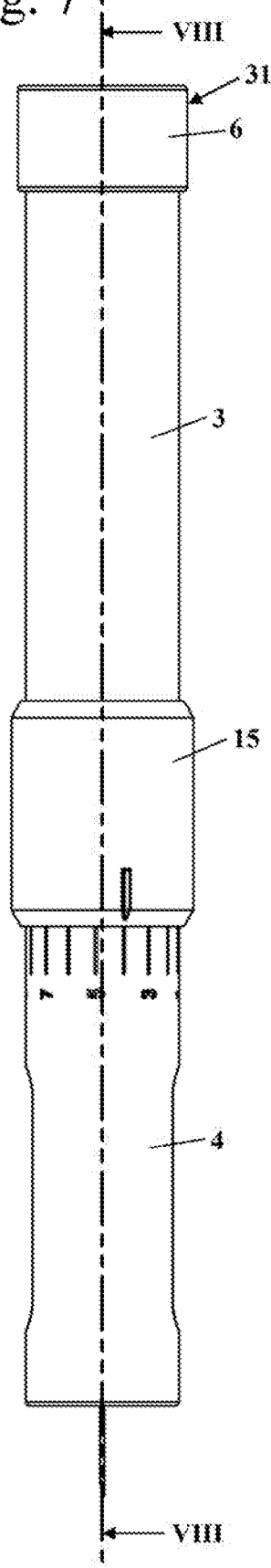
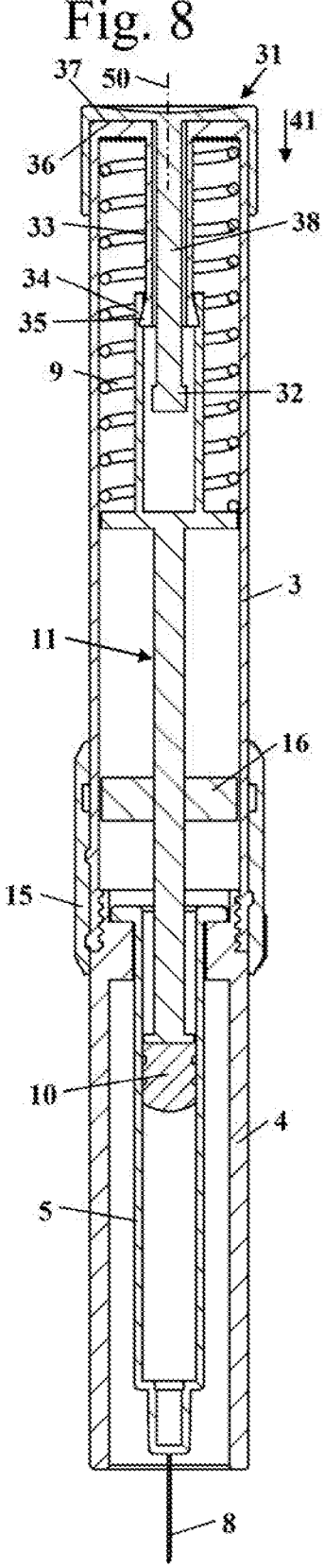
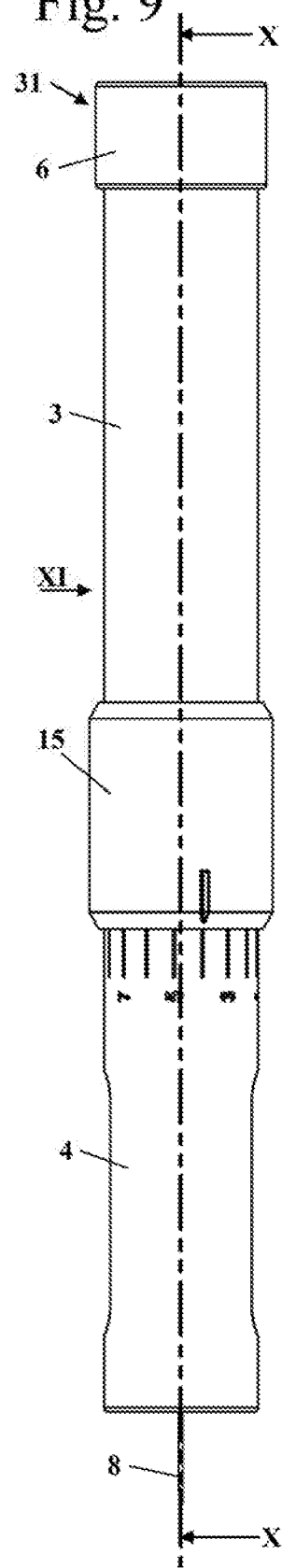

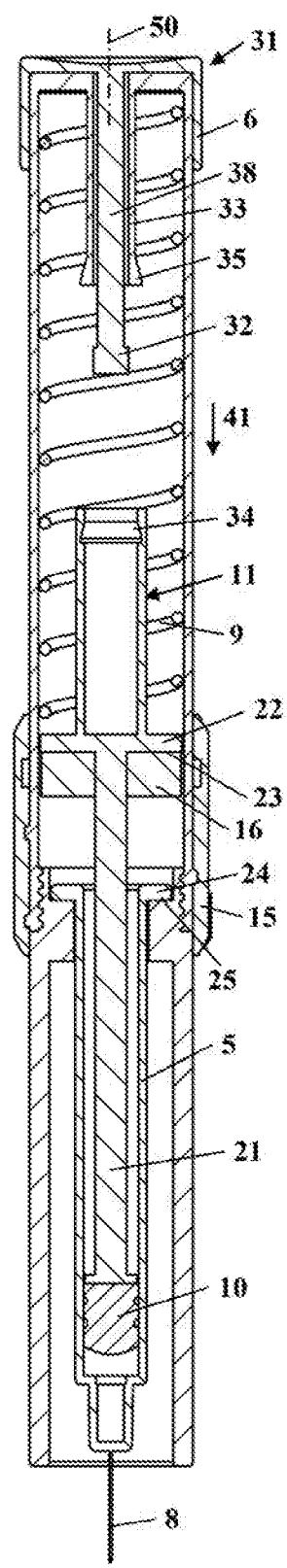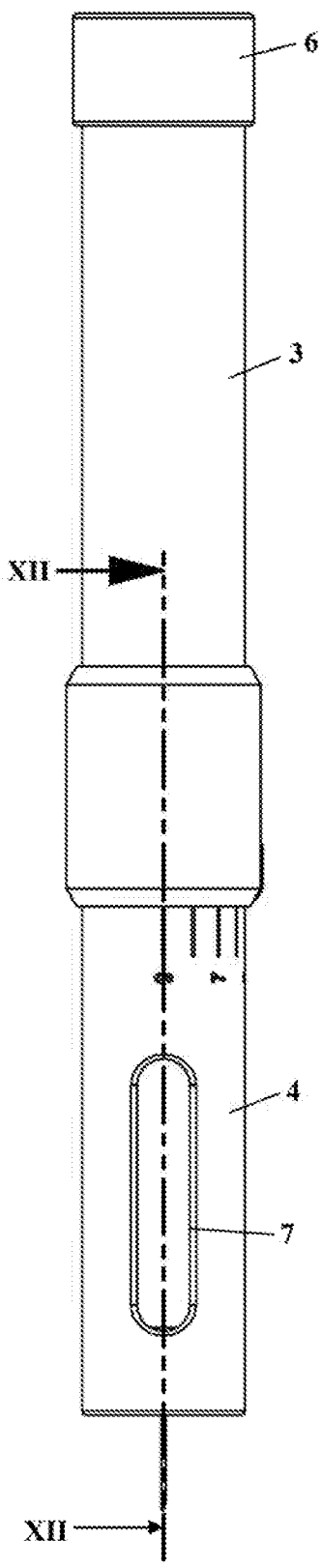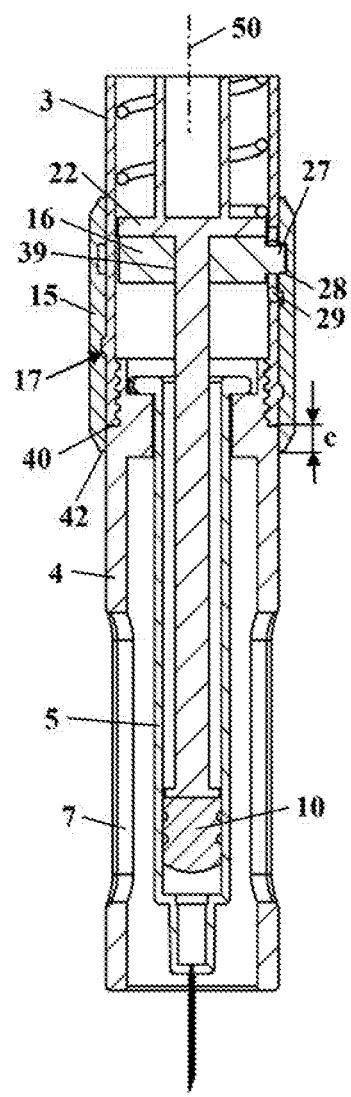

Fig. 13
Fig. 14
Fig. 15
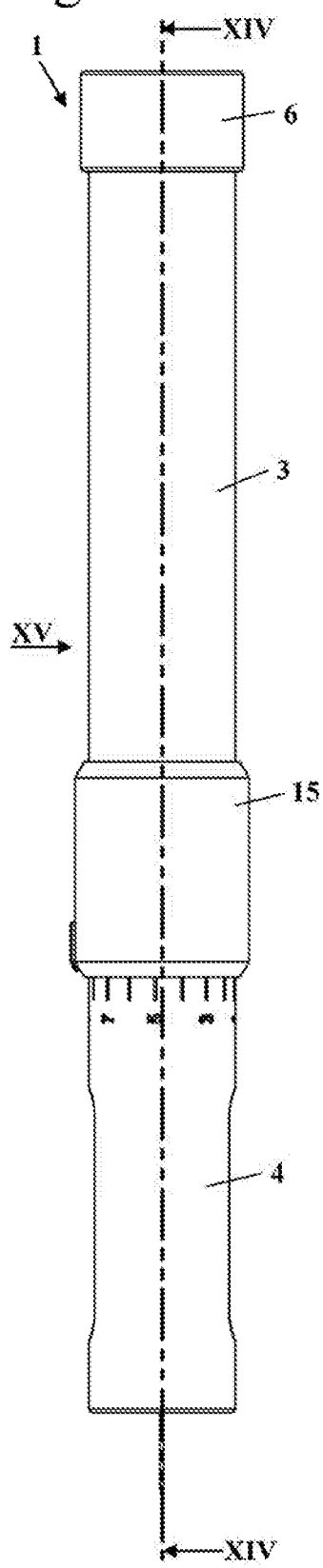
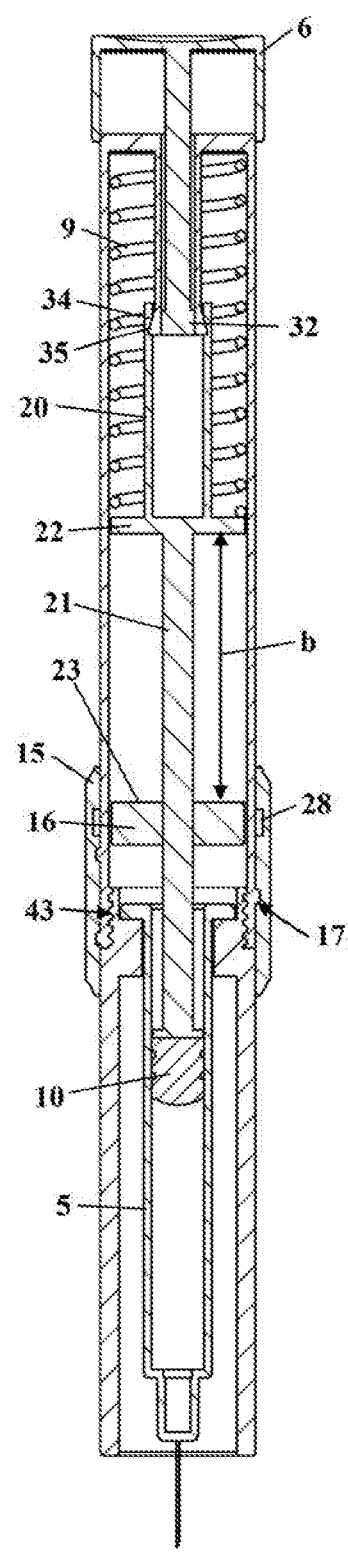
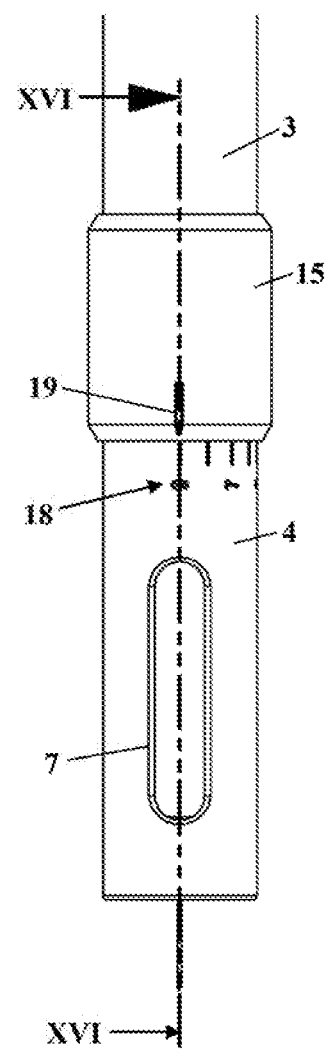

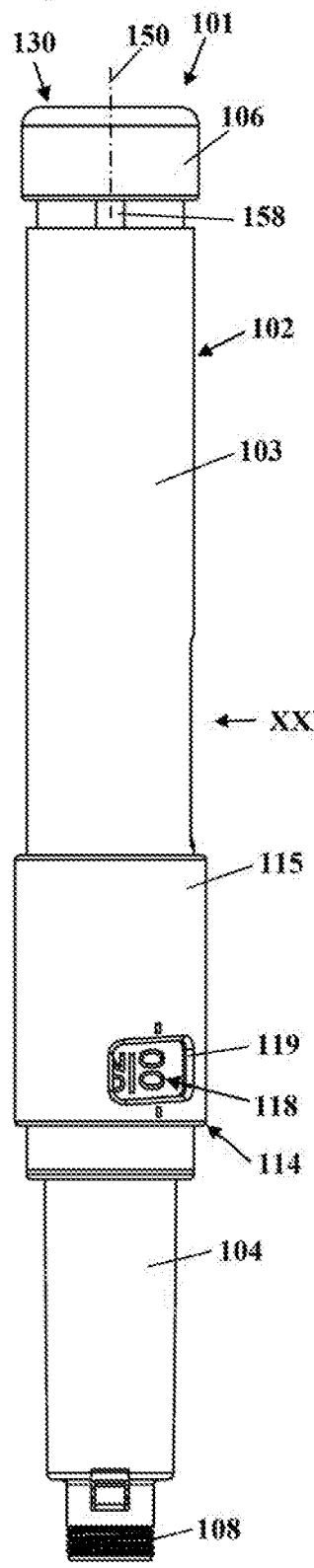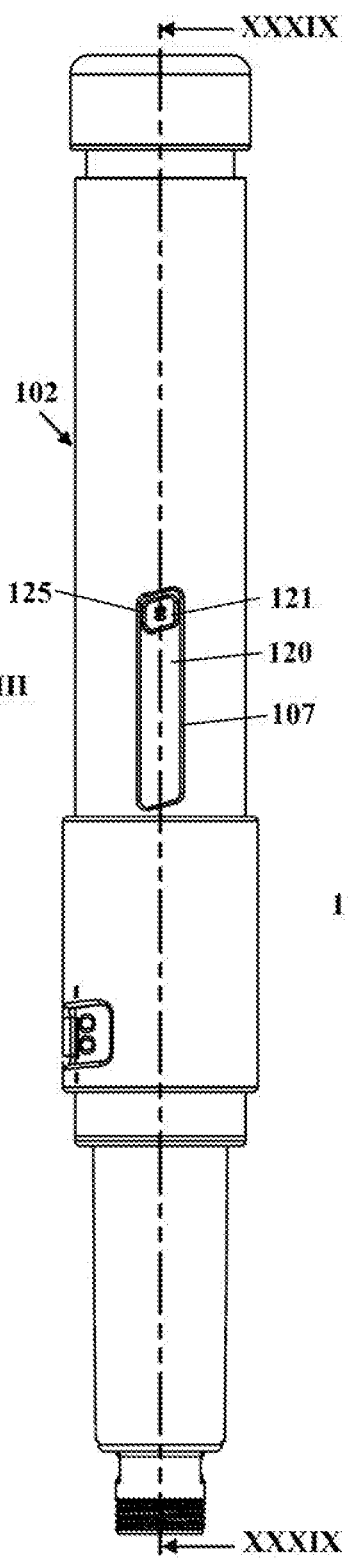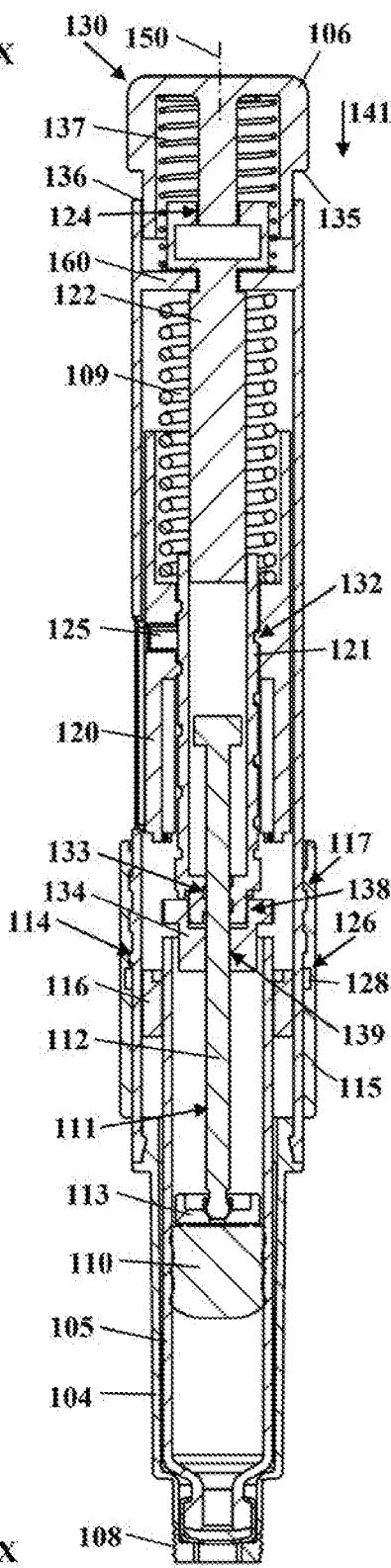

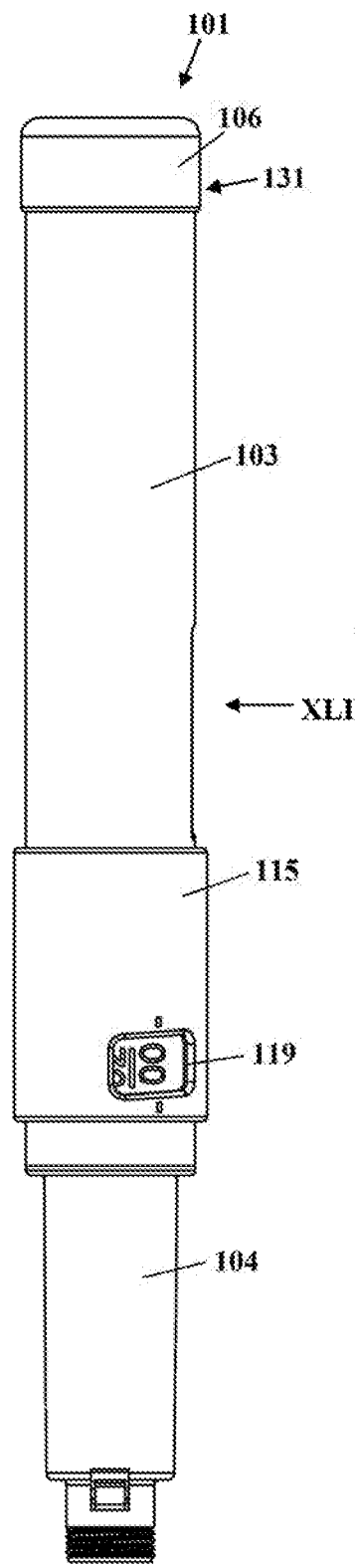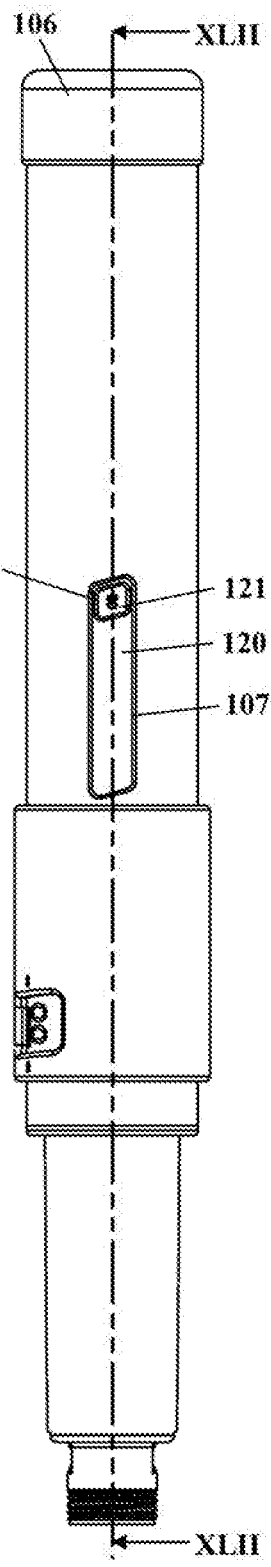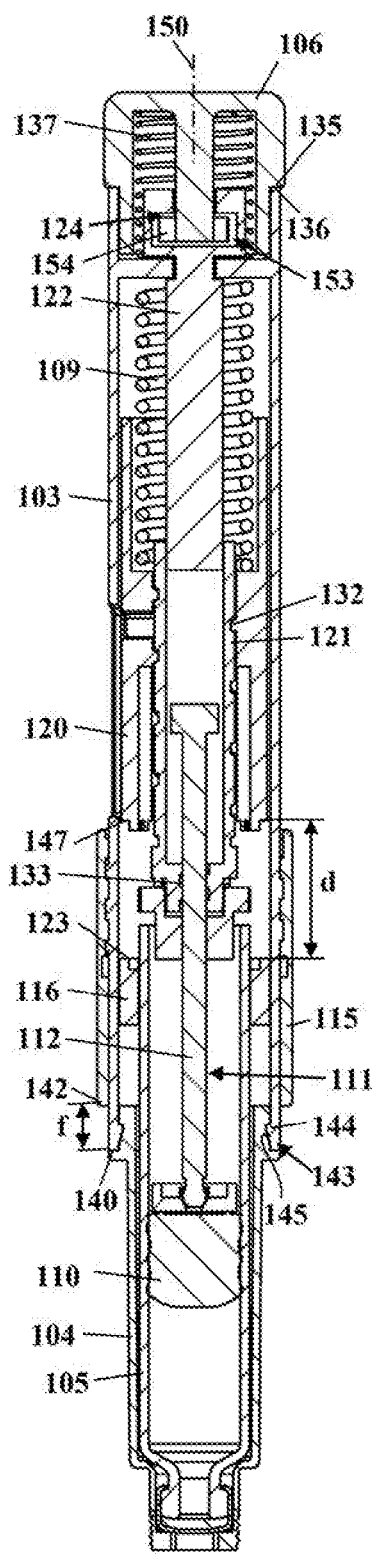

Fig. 43
Fig. 44
Fig. 45
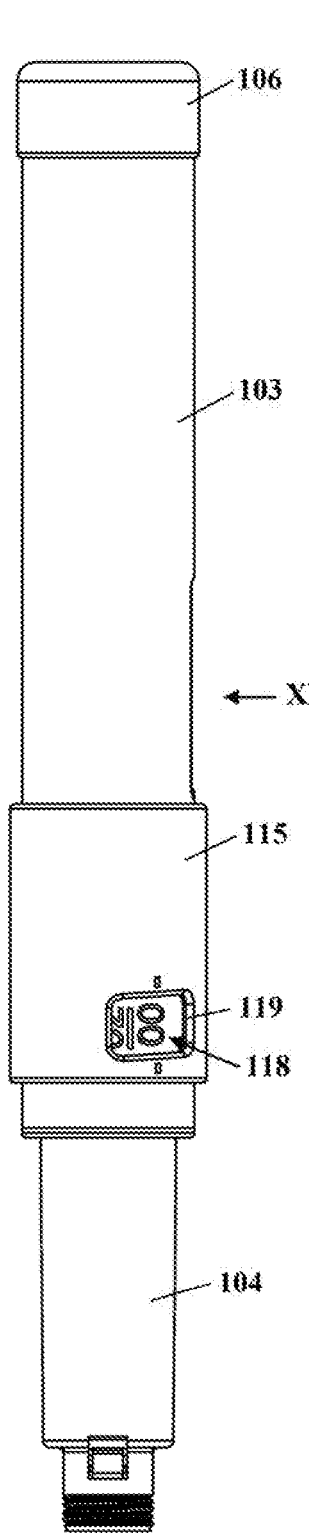
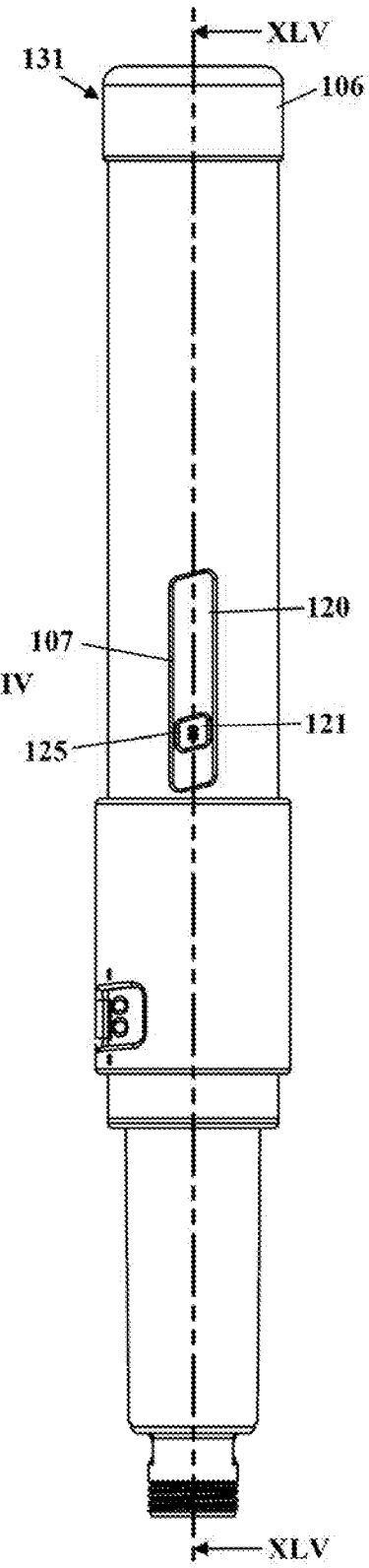
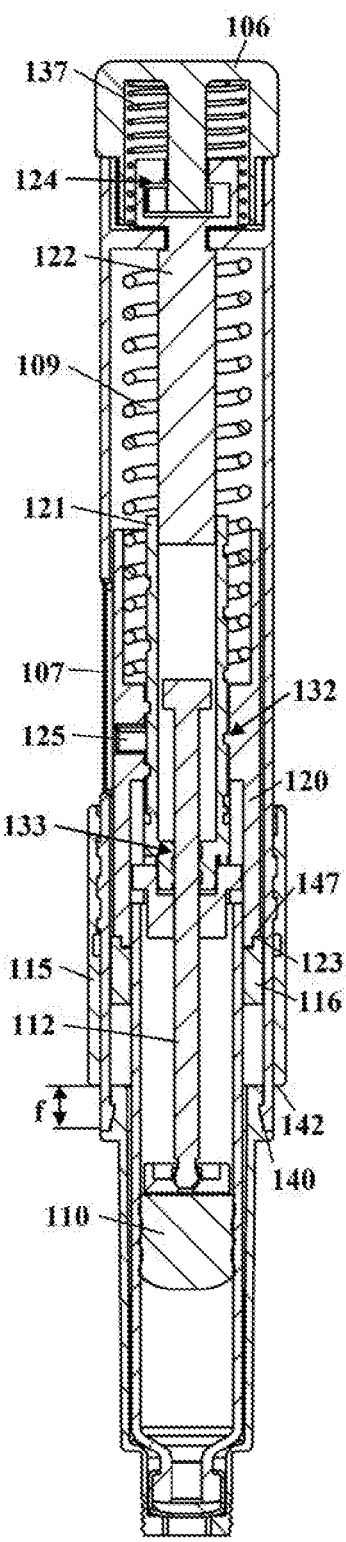

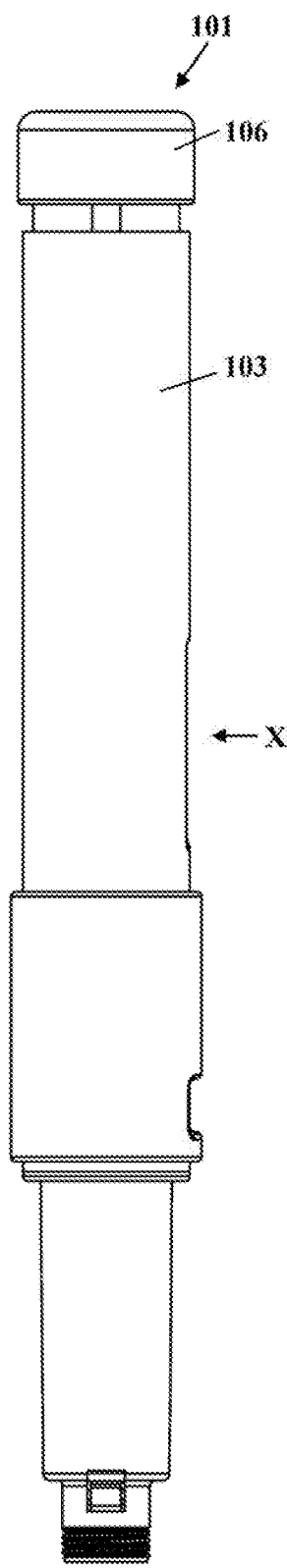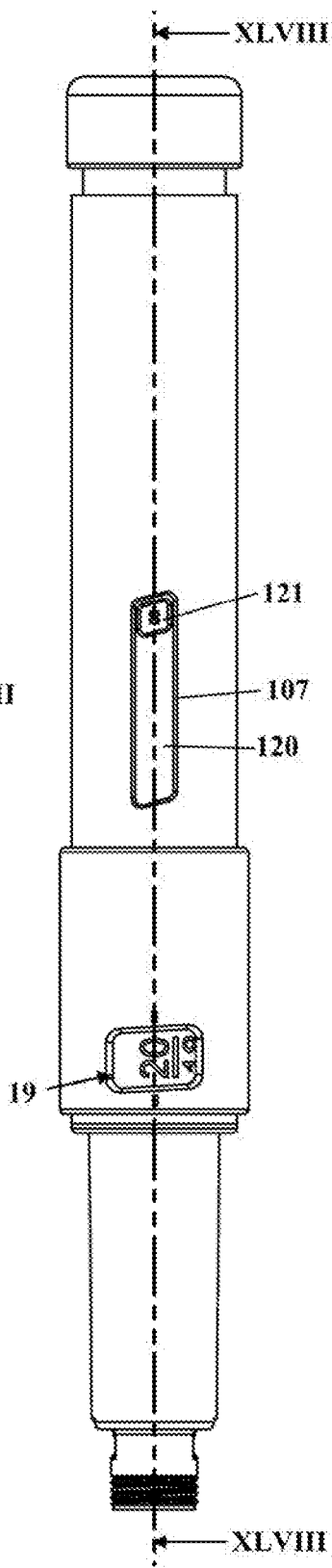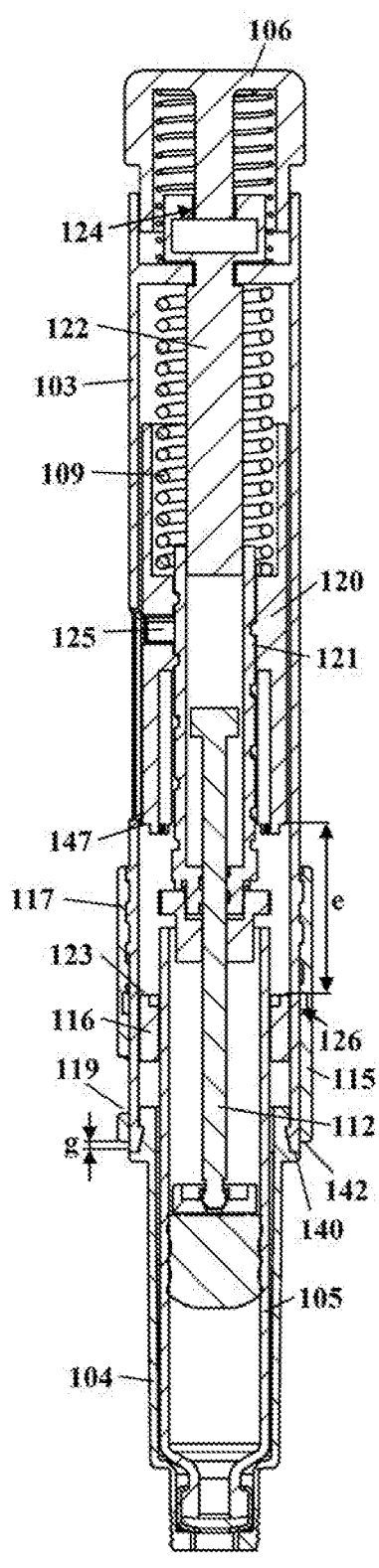

INJECTION DEVICE

CROSS REFERENCE TO RELATED APPLICATIONS

This application is a continuation application of international patent application PCT/EP2016/001696, filed Oct. 12, 2016 designating the United States and claiming priority from German application 20 2015 007 351.4, filed Oct. 22, 2015, and the entire content of both applications is incorporated herein by reference.

FIELD OF THE INVENTION

The invention relates to an injection device for automatically squeezing injection liquid from a container.

BACKGROUND OF THE INVENTION

Automatic injection devices usually have a spring which causes the squeezing of the injection liquid from the container. Injection devices of this type are, for example, autoinjectors which serve for the one-shot squeezing of a dosage of injection liquid from a syringe. In the case of autoinjectors of this type, the entire injection liquid is squeezed in a single injection procedure. Different injection devices are to be chosen for different dosages of injection liquid to be dispensed.

An injection device which is to be manually activated is known from WO 2013/117332 A1, in the case of which the quantity of injection liquid to be squeezed is to be set by the operator prior to the injection. Herein, an injection sleeve is adjusted from a stop by a predefined path in the distal direction. When squeezing injection liquid, the operator pushes the operating element and, on account thereof, displaces the injection sleeve in the proximal direction until the latter reaches the stop. Depending on the quantity of injection liquid to be squeezed, dissimilar starting positions for the injection sleeve result on account thereof. The terminal position of the injection sleeve which corresponds to the terminal position of a metering piston which squeezes the injection liquid is fixedly predefined.

SUMMARY OF THE INVENTION

It is an object of the invention to provide an injection device for automatically squeezing injection liquid from a container, which has a simple construction and permits a setting of the quantity of injection liquid to be squeezed.

It is provided that the injection device has a setting device for setting the quantity of injection liquid to be squeezed. The injection device has an end stop which establishes the terminal position of the metering piston. The terminal position of the metering piston can herein be established directly on the metering piston per se, or indirectly by way of components which are coupled to the metering piston. A simple construction of the injection device is achieved in that the setting device has means for adjusting the position of the end stop. The terminal position of the metering piston can thus be set by way of the setting device. The starting position of the metering piston is the same for each quantity of injection liquid to be squeezed. On account thereof, the operator when setting does not have to move the metering piston, and the injection spring can be disposed in an already pretensioned manner in the housing of the injection device. This is advantageous in particular in the case of highly viscous injection liquids which require an injection spring that is conceived so as to be very strong. On account thereof, the injection spring does not have to be tensioned by the operator, but is tensioned in the production of the injection device. On account of the setting device acting on the position of the end stop, a setting of the quantity of injection liquid to be squeezed is nevertheless possible. The injection device is advantageously an injection device for the one-shot squeezing of injection liquid from a container. The injection device is disposed of after the one-shot squeezing of injection liquid. Such injection devices that are provided for a single injection are provided in particular for injecting medications which have to be injected only at large temporal intervals, the storage life of the injection liquid being shorter than the temporal interval between two injections.

The setting device advantageously adjusts the position of the end stop in a direction along a longitudinal central axis of the injection device. This enables a simple construction.

The setting device advantageously includes a stop element disposed in the housing and a setting ring which at least in part protrudes onto the housing external side and is to be activated by the operator. The operator can set the position of the stop element on the setting ring. The setting ring herein is advantageously rotatably mounted and, for setting the quantity of injection liquid to be squeezed, is rotated about the longitudinal central axis of the injection device by the operator. A simple construction is achieved when the setting ring is connected to the housing by way of a threaded connection, and a rotation of the setting ring causes a movement of the setting ring in the direction along the longitudinal central axis of the injection device. A very exact setting of the quantity of injection liquid to be squeezed can be achieved by a corresponding layout of the threaded connection.

The injection device advantageously includes a coupling installation which couples the axial position of the stop element to the axial position of the setting ring. The coupling installation advantageously includes at least one coupling element which protrudes through an opening in the housing into a guide of the coupling installation. The coupling element is advantageously secured on the stop element, and the guide is disposed on the setting ring. The stop element is advantageously guided so as to be rotationally fixed in the housing. The guide is formed in particular by an encircling groove of the setting ring. On account of the stop element being guided so as to be rotationally fixed in the housing, the opening in the housing through which the coupling element protrudes can be configured so as to be comparatively narrow in the circumferential direction, since the coupling element is not conjointly rotated when setting the quantity of injection liquid to be squeezed. On account thereof, a minor weakening of the housing in the region of the coupling element, and on account thereof a high stability of the injection device, is achieved. A simple construction results at the same time. The coupling element by way of the opening advantageously causes the rotationally-fixed guiding of the stop element. Additional means for guiding the stop element in a rotationally-fixed manner are not required on account thereof.

The injection device is advantageously an injection device in which the metering piston has a periphery which interacts with the end stop. An injection device of this type can be, for example, an autoinjector which serves for squeezing injection liquid from a syringe. The injection spring herein is advantageously supported on the distal side of the periphery. On account thereof, a simple construction of the injection device having a low number of components is achieved. The injection spring can be held so as to be already pretensioned in the housing.

Alternatively, it is advantageously provided that the injection device has an injection sleeve which is mounted so as to be rotationally fixed in the housing and which by way of a first threaded connection is connected to a metering member that is mounted so as to be rotatable and axially non-displaceable in the housing. The metering member by way of a second threaded connection is advantageously connected to the metering piston. The injection sleeve advantageously has a stop surface which interacts with the end stop. The end stop thus does not interact directly with the metering piston but establishes the terminal position of the metering piston indirectly by way of the injection sleeve, the metering member, and the two threaded connections. The injection spring by way of the proximal end thereof is advantageously supported on the injection sleeve. In the case of an injection device which has an injection sleeve and a metering member, a scale visible to the operator, by way of which the quantity of the already squeezed injection liquid is advantageously indicated, is advantageously attached to the metering member. This is advantageous in particular in the case of injection devices in which the operator can interrupt the injection and continue the latter, for example after a break that is pleasant to the operator.

A scale from which the position of the end stop and thus the set quantity of injection liquid to be squeezed can be derived is advantageously provided on the setting ring.

BRIEF DESCRIPTION OF THE DRAWINGS

The invention will now be described with reference to the drawings wherein:

FIG. 1 shows a lateral view of an injection device in a first position in which a first quantity of injection liquid to be squeezed is set;

FIG. 2 shows a section along the line II-II in FIG. 1;

FIG. 3 shows a lateral view of the injection device in the direction of the arrow III in FIG. 1;

FIG. 7 shows a lateral view of the injection device after the displacement of the operating element in the proximal direction;

FIG. 8 shows a section along the line VIII-VIII in FIG. 7;

FIG. 9 shows a lateral view of the injection device after the squeezing of the injection liquid;

FIG. 10 shows a section along the line X-X in FIG. 9;

FIG. 11 shows a lateral view in the direction of the arrow XI-XI;

FIG. 12 shows a fragmented sectional illustration along the line XII-XII in FIG. 11;

FIG. 13 shows a lateral view of the injection device prior to the injection procedure, having a second, maximum, set quantity of injection liquid;

FIG. 14 shows a section along the line XIV-XIV in FIG. 13;

FIG. 15 shows a fragmented lateral view in the direction of the arrow XV in FIG. 13;

FIG. 37 shows a lateral view of an injection device;

FIG. 38 shows a lateral view in the direction of the arrow XXXVIII in FIG. 37;

FIG. 39 shows a section along the line XXXIX-XXXIX in FIG. 38;

FIG. 40 shows a lateral view of the injection device after the displacement of the operating element in the proximal direction;

FIG. 41 shows a lateral view in the direction of the arrow XLI in FIG. 40;

FIG. 42 shows a section along the line XLII-XLII in FIG. 41;

FIG. 43 shows a lateral view of the injection device after the injection procedure;

FIG. 44 shows a lateral view in the direction of the arrow XLIV in FIG. 43;

FIG. 45 shows a section along the line XLV-XLV in FIG. 44;

FIG. 46 shows a lateral view of the injection device prior to the injection procedure, having a second set quantity of injection liquid to be squeezed;

FIG. 47 shows a lateral view in the direction of the arrow XLVII in FIG. 46;

FIG. 48 shows a section along the line XLVIII-XLVIII in FIG. 47;

DESCRIPTION OF THE PREFERRED EMBODIMENTS OF THE INVENTION

Figure 4:
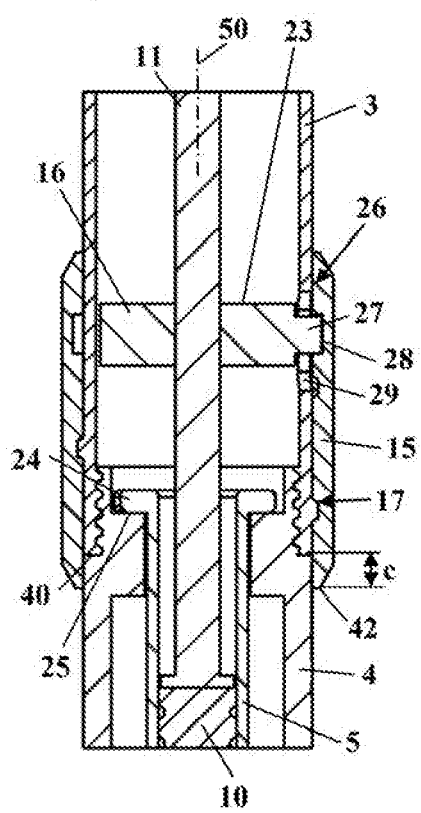
FIG. 4 shows an enlarged sectional illustration along the line IV-IV in FIG. 3.

FIG. 1 shows an injection device 1 which is provided for the one-shot automatic squeezing of a dosage of injection liquid from a container, the latter a syringe in the embodiment. Injection devices of this type are also referred to as autoinjectors. The injection device 1 has a housing 2 which includes an upper, distal housing part 3 and a lower, proximal housing part 4. A setting ring 15 is mounted so as to be rotatable on the upper housing part 3. The setting ring 15 serves for setting the quantity of injection liquid to be squeezed. This is advantageous in particular for injection liquids in the case of which the required quantity depends on the body weight of the user, for example. On account of the operator being able to set the quantity of injection liquid to be squeezed within limits predefined by the construction, a separate injection device does not have to be kept ready for every possible quantity of injection liquid. The setting ring 15 carries a marking 19 which on a scale 18 that is applied to the lower housing part 4 indicates the set quantity of injection liquid to be squeezed. An operating element 6 is disposed on the distal end of the upper housing part 3. A safety cap 12 which covers an injection needle 8 (FIG. 2) of the injection device 1 is disposed on the proximal end.

The distal end of the injection device 1 is that end that faces away from the injection needle 8. "Proximal" refers to that side of the injection device 1 which in an injection faces the pierced location, and "distal" refers to that side which faces away from the pierced location. The proximal direction refers to the injection direction, thus the direction toward the injection needle or the direction in which the injection liquid is squeezed from the container, respectively. The distal direction refers to the opposite direction, thus away from the injection needle 8.

FIG. 2 shows the construction of the injection device 1 in detail. A container 5 having injection liquid is disposed in the lower housing part 4. The container 5 in the embodiment is a syringe which by way of the distal periphery 24 thereof is supported on a shoulder 25 of the lower housing part 4. The injection needle 8 is surrounded by a needle protector 13 which is fixedly connected to the safety cap 12 and which, when the safety cap 12 is pulled off, is likewise pulled off. A plug 10 on which a metering piston 11 of the injection device 1 bears is disposed in the container 5. The metering piston 11, when squeezing injection liquid, moves in the proximal direction and, on account thereof, displaces the plug 10 in the proximal direction such that injection liquid is squeezed. The metering piston 11 has a piston rod 21 which protrudes in the proximal direction, and a sleeve portion 20 which has an approximately cylindrical shape and protrudes in the distal direction. A periphery 22 running transversely to the longitudinal central axis 50 of the injection device 1 is formed between the sleeve portion 20 and the piston rod 21, the periphery 22 in the embodiment having the form of a disk. The sleeve portion 20 at the distal end thereof has a depression 34 into which locking elements 35 of the operating element 6 protrude. The locking elements 35 are configured in the embodiment on holding arms 33 of the upper housing part 3. The holding arms 33 extend parallel with a longitudinal central axis 50 of the injection device 1. A blocking portion 32 of the operating element 6 is disposed radially within the locking elements 35. The blocking portion 32 is configured such that the locking elements 35 cannot move from the depression 34 in a radially inward manner. On account thereof, the locking elements 35 fix the metering piston 11 in the position shown in FIG. 2, such that the metering piston 11 cannot move in the proximal direction.

An injection spring 9, which by way of the distal end thereof is supported on a distal wall 36 of the upper housing part 3, and by way of the proximal end thereof is supported on the periphery 22 of the metering piston 11, is disposed in the upper housing part 3. The injection spring 9 is pretensioned. As soon as the locking elements 35 release the metering piston 11, the injection spring 9 pushes the metering piston 11 in the proximal direction such that injection liquid is automatically squeezed.

The injection device 1 has a setting device 14 for setting the quantity of injection liquid to be squeezed. The setting device 14 includes the setting ring 15. In the position shown in FIGS. 1 and 2, the marking 19 points to the value 4 of the scale 18. This means that four units of injection liquid are squeezed in addition to a basic dosage. The setting device 14 includes a stop element 16 which is disposed within the housing 2 and in the embodiment is configured as a disk. The stop element 16 has a centric opening 39 through which the piston rod 21 protrudes. An end stop 23 for the periphery 22 is formed on the distal side of the stop element 16. The end stop 23 in the embodiment is formed by the entire distal end side of the stop element 16. As is also shown in FIG. 2, the setting ring 15 is held on the housing 2 by way of a threaded connection 17. The setting ring 15 on the internal side thereof, at the height of the stop element 16, has a guide 28 which is configured as a groove and the function thereof will be explained in yet more detail hereunder. As is shown in FIG. 2, the periphery 22 has a spacing a from the end stop 23, the spacing a being measured in the axial direction.

As is shown in FIG. 2, the upper housing part 3 and the lower housing part 4 in the embodiment are interconnected by way of a threaded connection 43. Another connection of the housing parts 3 and 4 can also be advantageous. The injection device 1 has two viewing windows 7 in the lower housing part 4, the container 5 being visible through the two viewing windows 7. One of the viewing windows 7 is shown in FIG. 3.

As is shown in FIG. 4, the setting ring 15 has a proximal end side 42. The upper housing part has a proximal end side 40. The end side 40 and the end side 42 at the set quantity of injection liquid have a mutual spacing c that is measured in the direction along the longitudinal central axis. FIG. 4 also shows a coupling installation 26 of the setting device 14 in detail. The coupling installation 26 couples the axial position of the stop element 16 to the axial position of the setting ring 15. The coupling installation 26 includes a pin 27 of the stop element 16 that protrudes through an opening 29 of the upper housing part 3 into the guide 28 of the setting ring 25. The extent of the pin 27 in the direction along the longitudinal central axis 50 in the embodiment herein corresponds to the height of the groove 28 such that the pin 27 is held largely without play in the guide 28. When the operator rotates the setting ring 15, the setting ring 15 by virtue of the threaded connection 17 thus moves in the direction along the longitudinal central axis 50. Depending on the direction of rotation, the setting ring 15 moves in the distal direction or in the proximal direction. By way of the guide 28 in which the pin 27 engages, the setting ring 15 in the axial movement thereof entrains the stop element 16. On account thereof, the position of the end stop 23 in the housing 2 is adjusted in the direction along the longitudinal central axis 50. A sensitive setting of the axial position of the stop element 16 and thus of the dosage to be squeezed is possible by virtue of the comparatively slight pitch of the threaded connection 17.

Figure 5:
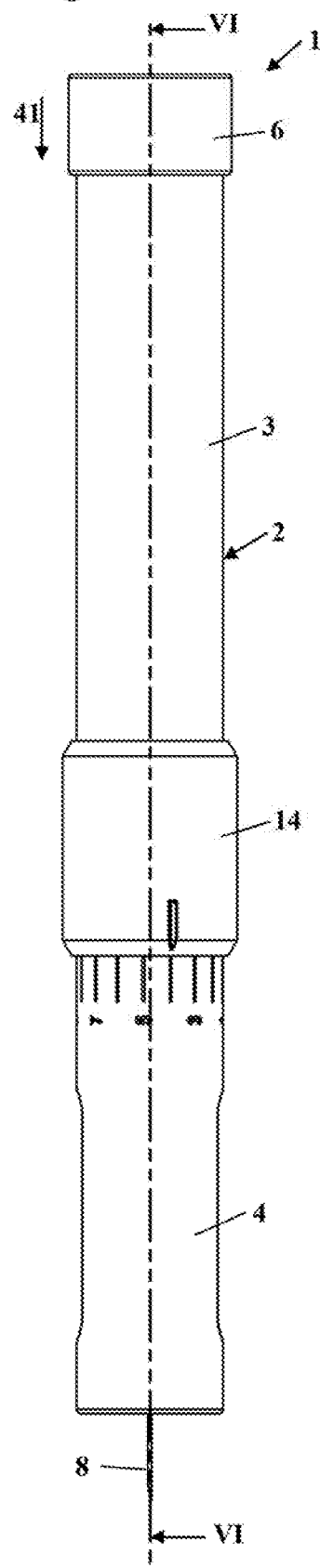
FIG. 5 shows a lateral view of the injection device after the removal of the safety cap.
Figure 6:
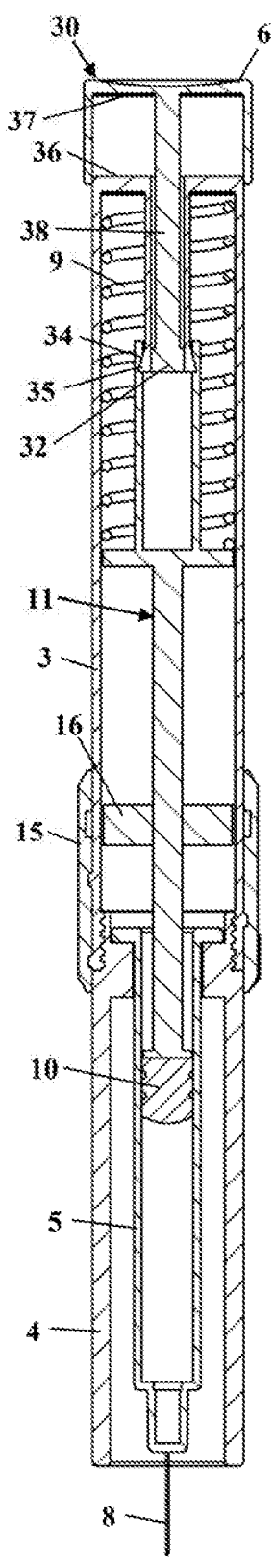
FIG. 6 shows a section along the line VI-VI in FIG. 5.

In order for an injection to be carried out, the operator, after setting the quantity of injection liquid to be squeezed, removes the safety cap 12. FIGS. 5 and 6 show the injection device 1 having the safety cap removed. The operating element 6 is pot-shaped, having a web-shaped connection portion 38 which protrudes into the interior of the upper housing part 3 and supports the blocking portion 32. The internal side 37 of the operating element 6, conjointly with the distal wall 36 of the upper housing part 3, forms a stop for the proximal position 31 of the operating element 6.

The operating element 6 in FIGS. 1 to 6 is in the distal position 30 thereof. In order for an injection to be released, the operating element 6 is to be moved in the proximal direction 41. This position is shown in FIGS. 7 and 8. The operating element 6 is in the proximal position 31 thereof. The internal side 37 of the operating element 6 bears on the distal wall 36 of the upper housing part 3. The blocking portion 32 has moved in the proximal direction 41. The connection portion 38 which on account of the movement in the proximal direction 41 has come into the region of the locking elements 35 is configured so as to be narrower than the blocking portion 32. On account thereof, the locking elements 35 in the proximal position 31 of the operating element 6 can pivot in a radially inward manner. The depression 34 and the locking elements 35 are configured so as to be beveled. The injection spring 9 exerts a force in the proximal direction 41 on the metering piston 11. This force causes a movement of the metering piston 11 in the proximal direction 41, wherein the locking elements 35 by way of the bevels are deflected in a radially inward manner. On account thereof, the metering piston 11 can freely move in the proximal direction 41, herein squeezing injection liquid from the container 5.

FIGS. 9 and 10 show the injection device 1 after the injection procedure. The operating element 6 is in the proximal position 31 thereof. The metering piston 11 is also in the proximal position thereof. The periphery 22 bears on the end stop 23 of the stop element 16. The plug 10 has not been completely pushed up to the proximal end of the container 5, such that a residual quantity of injection liquid is still disposed in the container 5. As is shown in FIGS. 11 and 12, the position of the stop element 16 in the housing 2 has not changed. The end sides 40 and 42 are also mutually spaced apart by the spacing c. The metering piston 11 by way of the periphery 22 and the pin 27 of the stop element 16 is supported in the guide 28 of the setting ring 15. The pitch of the threaded connection 17 is so minor that the pin 27 cannot cause any displacement of the setting ring 15 in the proximal direction.

FIGS. 13 to 16 show the injection device having a second set quantity of injection liquid to be squeezed. The second quantity of injection liquid to be squeezed corresponds to nine additional units of injection liquid, thus to the maximum dosage of the injection device 1 that can be set.

Figure 16:
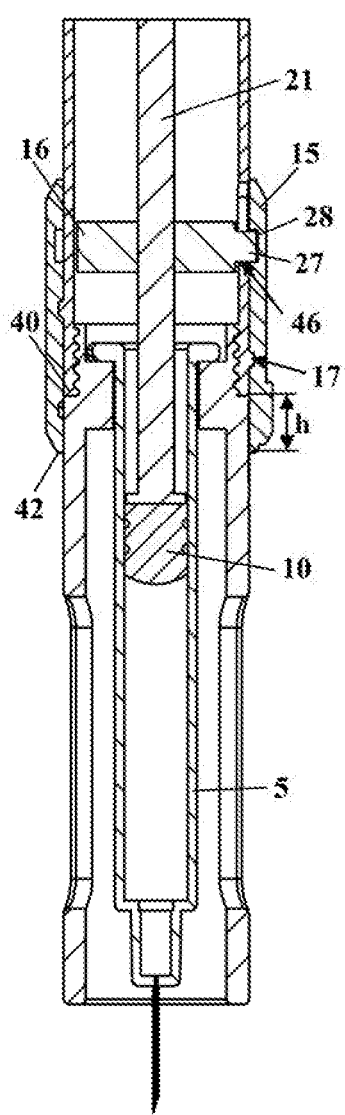
FIG. 16 shows a section along the line XVI-XVI in FIG. 15.
Figure 17:
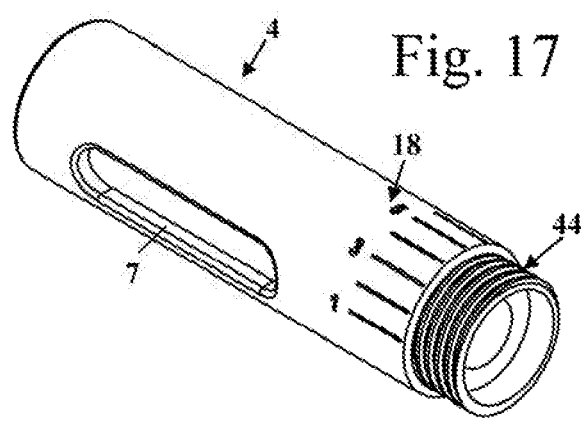
FIG. 17 shows a perspective illustration of a lower housing part of the injection device.
Figure 18:
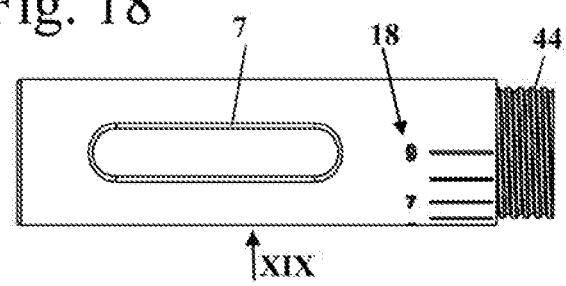
FIG. 18 shows a lateral view of the lower housing part.
Figure 19:
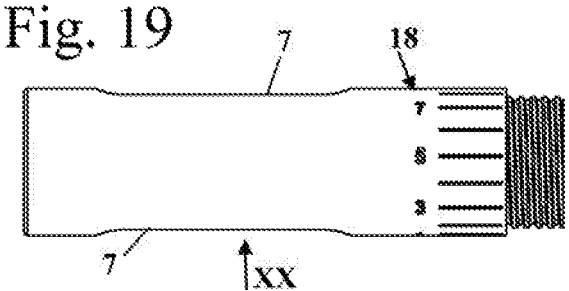
FIG. 19 shows a lateral view in the direction of the arrow XIX in FIG. 18.
Figure 20:
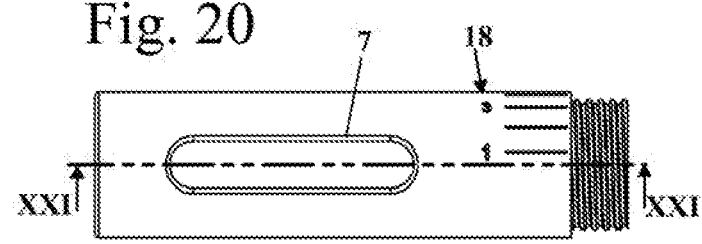
FIG. 20 shows a lateral view in the direction of the arrow XX in FIG. 19.

As is shown in FIG. 14, the periphery 22 at the set dosage of nine additional units has a spacing b from the end stop 23. The spacing b herein is larger than the spacing a (FIG. 2) at the first set dosage of four additional units. The stop element 16 has moved in the proximal direction in relation to the position of the stop element 16 shown in FIG. 2. As is shown in FIG. 16, the end side 40 of the upper housing part 3 in this position has a spacing h from the proximal end side 42 of the setting ring 15, the spacing h being larger than the spacing c at the first set dosage (FIG. 12). On account thereof, the metering piston 11 at the second set dosage can move further in the distal direction and, on account thereof, squeeze a larger quantity of injection liquid from the container 5. The proximal end of the opening 29 forms a first, proximal stop 46 for the pin 27. As is shown in FIG. 16, the pin 27 at the maximum set quantity of injection liquid bears on the stop 46.

Figure 21:
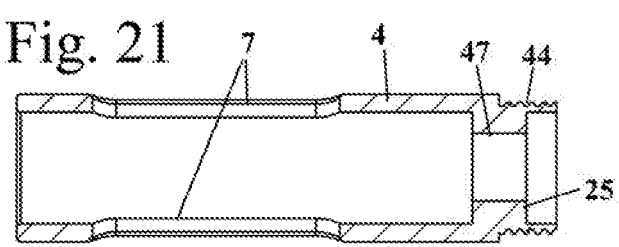
FIG. 21 shows a section along the line XXI-XXI in FIG. 20.
Figure 22:
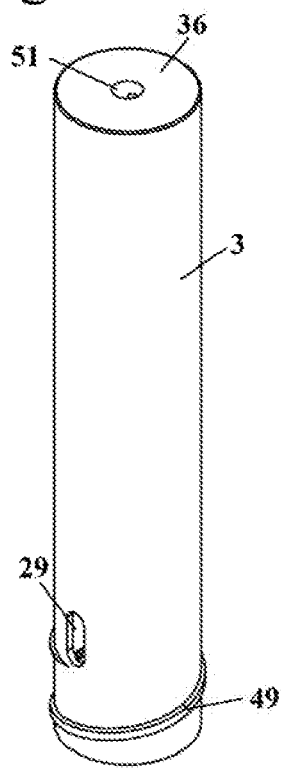
FIG. 22 shows a perspective illustration of an upper housing part of the injection device.
Figure 23:
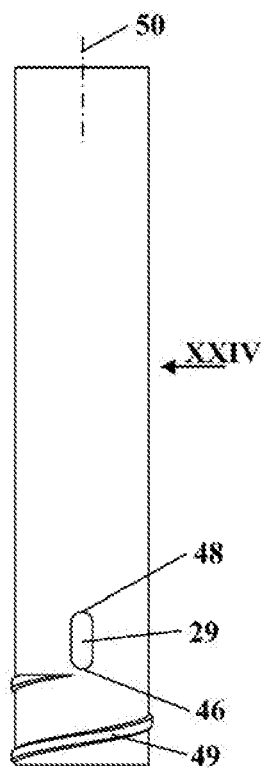
FIG. 23 shows a lateral view of the upper housing part.
Figure 24:
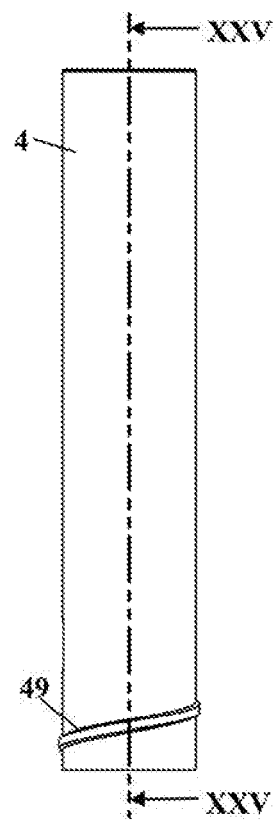
FIG. 24 shows a lateral view in the direction of the arrow XXIV in FIG. 23.

FIGS. 17 to 21 show the construction of the lower housing part 4 in detail. As is shown in the FIGS., the upper housing part 4 on the distal side thereof, shown on the right in FIGS. 18 to 21, has an external thread 44 which is part of the threaded connection 43 to the upper housing part 3. The scale 18 is also shown in detail in FIGS. 18 to 20. The scale 18 in the embodiment runs from 1 to 9 such that one to nine additional units of injection liquid can be injected by way of the setting device 14. The size of a unit depends on the pitch of the threaded connection 17. As is shown in FIG. 21, the upper housing part 21, adjacent to the shoulder 25, has a receptacle opening 47 for the container 5.

Figure 25:
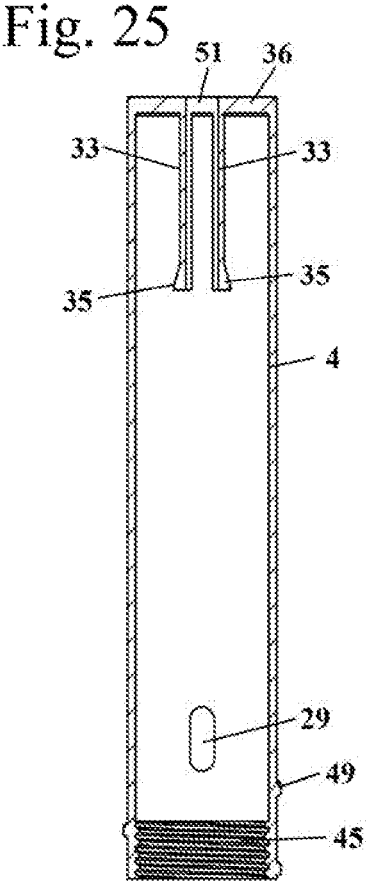
FIG. 25 shows a section along the line XXV-XXV in FIG. 24.

FIGS. 22 to 25 show the upper housing part 3 in detail. The distal wall 36 has a passage opening 51 for the connection portion 38 of the operating element 6. The opening 29 is also visible in FIGS. 22 and 23. The opening 29 is configured as an elongate hole which extends parallel with the longitudinal central axis 50. The proximal end of the opening 29 forms the first, proximal stop 46 for the pin 27. The stop 46 delimits the maximum quantity of injection liquid to be squeezed. The distal end of the opening 29 forms a second, distal stop 48 for the pin 27, establishing the minimal quantity of injection liquid to be squeezed that can be set. As is shown in FIGS. 22 to 25, the upper housing part 3 at the distal end thereof supports an external thread 49 which is part of the threaded connection 17. As is shown in FIG. 25, an internal thread 45 is also provided at the distal end, the internal thread 45, conjointly with the external thread 44 of the lower housing part 4, forming the threaded connection 43 between the two housing parts 3 and 4. The configuration of the two holding arms 33 which extend from the internal side of the wall 36 in the proximal direction is also shown in FIG. 25. The holding arms 33 are disposed on the circumference of the passage opening 52.

Figure 26:
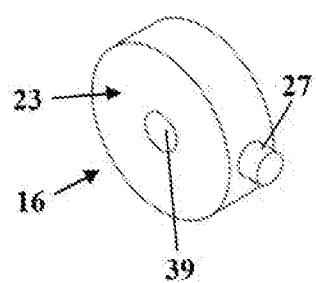
FIG. 26 shows a perspective illustration of a stop element of the injection device.
Figure 27:
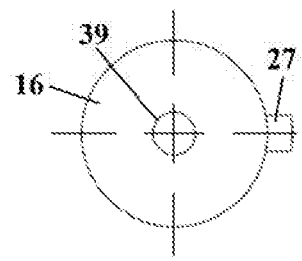
FIG. 27 shows a lateral view of the stop element.
Figure 28:
FIG. 28 shows a lateral view in the direction of the arrow XXVIII in FIG. 27.

FIGS. 26 to 28 show the configuration of the stop element 16 in detail. The stop element 16 is configured as a disk, the distal side of the latter forming the end stop 23. The pin 27 in the embodiment is configured so as to be cylindrical and protrudes in a radially outward manner. Another configuration of the coupling element, in particular an angular configuration, can however also be advantageous.

Figure 29:
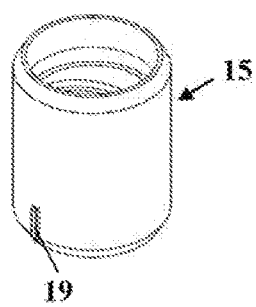
FIG. 29 shows a perspective illustration of a setting ring of the injection device.
Figure 30:
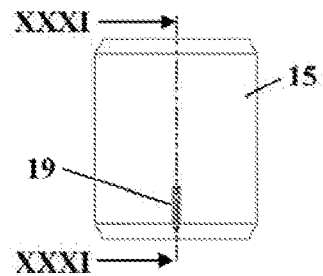
FIG. 30 shows a lateral view of the setting ring.
Figure 31:
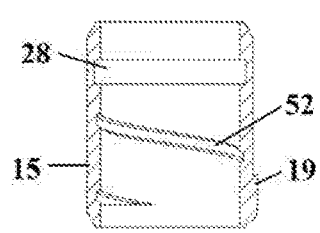
FIG. 31 shows a section along the line XXXI-XXXI in FIG. 30.

FIGS. 29 to 31 show the configuration of the setting ring 15. The setting ring 15 is configured so as to be sleeve-shaped and is disposed completely on the external side of the housing 2. However, it can also be provided that the setting ring 15 extends through the opening 29 to the stop element 16. However, the opening 29 in this instance must have a correspondingly large extent in the circumferential direction, this potentially leading to a reduction in the stability of the housing 2. The setting ring 15 has an internal thread 52 which, conjointly with the external thread 49 of the upper housing part 3, forms the threaded connection 17. The setting ring 15 in the distal region thereof, on the internal circumference thereof, has the guide 28 which is configured as an encircling groove. The height of the guide 28 corresponds to the height of the pin 27 such that a setting of the quantity of injection liquid to be squeezed is possible without play. However, play between the guide 28 and the pin 27 can also be provided, since the position of the pin 27 in the guide 28 at the end of the injection is predefined by virtue of the force of the injection spring 9.

Figure 32:
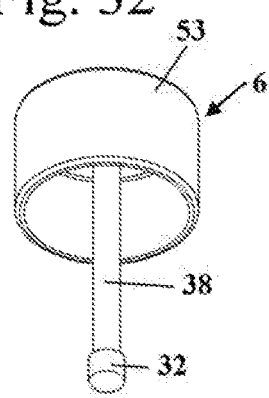
FIG. 32 shows a perspective illustration of an operating element of the injection device.
Figure 33:
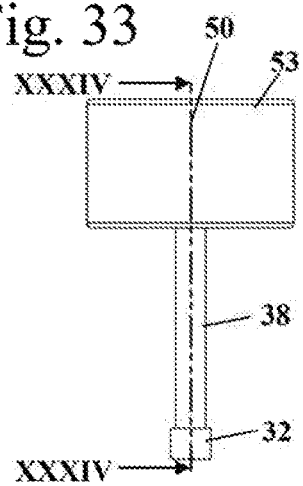
FIG. 33 shows a lateral view of the operating element.
Figure 34:
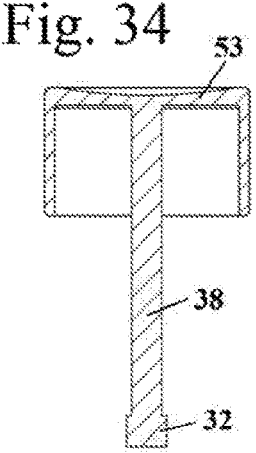
FIG. 34 shows a section along the line XXXIV-XXXIV in FIG. 33.

As is shown in FIGS. 32 to 34, the operating element 6 on the distal side thereof has an activation portion 53 which extends so as to be approximately perpendicular to the longitudinal central axis 50 and on which the operator can push the operating element 6 in the proximal direction 41 (FIG. 8). The connection portion 38 is configured so as to be bar-shaped and protrudes from the center of the activation portion 53 in the proximal direction. The connection portion 38 and the blocking portion 32 are in each case configured so as to be cylindrical, wherein the external diameter of the blocking portion 32 is larger than that of the connection portion 38.

Figure 35:
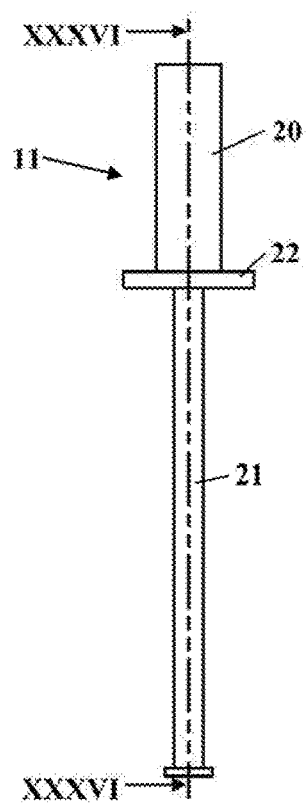
FIG. 35 shows a lateral view of a metering piston of the injection device.
Figure 36:
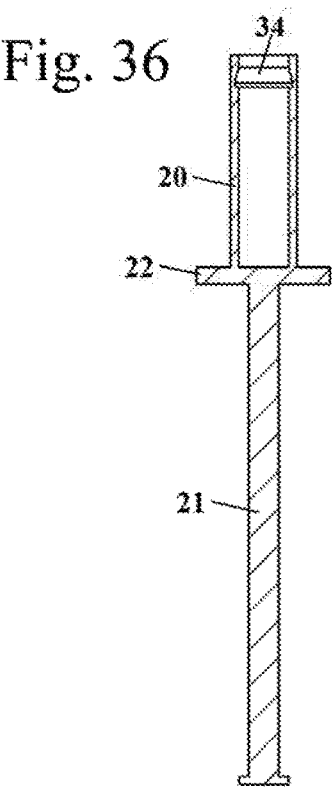
FIG. 36 shows a section along the line XXXVI-XXXVI in FIG. 35.

FIGS. 35 and 36 show the metering piston 11. The sleeve portion 20 on the distal end thereof, on the internal side thereof, has the depression 34 which in the embodiment is configured as an encircling groove. However, it can also be provided that a separate depression 34 is configured on the metering piston 11 for each locking element 35. The configuration and number of locking elements 35 can be conceived so as to be adapted to the force exerted by the injection spring 9.

FIGS. 37 to 80 show a second embodiment of an injection device 101. The injection device 101 has a housing 102 which includes an upper, distal housing part 103 and a lower, proximal housing part 104. An operating element 106 which in FIGS. 37 to 39 is in the distal position 130 thereof is disposed on the distal side of the upper housing part 103. The injection device 101 at the proximal end thereof has a needle receptacle 108 on which an injection needle can be fixed. In order to set the quantity of injection liquid to be squeezed, the injection device 101 has a setting device 114 which includes a setting ring 115 that is mounted so as to be rotatable on the external side of the housing 102. The setting ring 115 has a viewing window 119 through which a scale 118 which is applied to the external side of the upper housing part 103 is visible.

As is shown in FIG. 38, the upper housing part 103 has a viewing window 107. The external side of an injection sleeve 120 that is disposed in the housing 102 is visible through the viewing window 107. The injection sleeve 120 has an opening 125 which is also shown in FIG. 39 and through which a metering member 121 which is disposed within the injection sleeve 120 is visible, the metering member 121 on the external side thereof supporting the scale 118.

As is shown in FIG. 39, a container 105, a vial in the embodiment, is disposed in the lower housing part 104. The injection device 101 is advantageously also provided for the one-shot squeezing of a dosage of injection liquid. A plug 110 on which a piston disk 113 of a metering piston 111 bears is disposed in the container 105. In order for injection liquid to be squeezed, the metering piston 111 is moved in the proximal direction 141 and, on account thereof, displaces the plug 110 such that injection liquid is squeezed. The metering piston 111 has a piston rod 112 which in a guide 139 is mounted so as to be rotationally fixed and axially displaceable in the housing 102. The guide 139 is configured on a bearing portion 134 of the housing 102. The metering member 121 by way of a threaded connection 133 is connected to the metering piston 111. The metering member 121 on the bearing portion 134 is mounted so as to be rotatable and axially fixed by way of a pivot bearing 138. The metering member 121 is connected to the injection sleeve 120 by way of a threaded connection 132. An injection spring 109, which by way of the distal end thereof is supported on an intermediate wall 160 of the upper housing part 3, and by way of the proximal end thereof is supported on the injection sleeve 120, is disposed in the housing 102. The injection spring 109 is advantageously already pretensioned such that the operator does not have to tension the injection spring 109. This is advantageous in particular when the injection liquid is highly viscous, such that the injection spring 109 has to be conceived to be very strong, and comparatively large forces are required for tensioning the injection spring 109.

The injection device 101 has an entrainment element 122 which is connected to the operating element 106 by way of a coupling 124. In the distal position 130 of the operating element 106, shown in FIG. 38, the operating element 106 and the entrainment element 122 are interconnected in a rotationally-fixed manner by way of the coupling 124. The entrainment element 124 is connected in a rotationally-fixed manner to the metering member 121. The operating element 106 by way of guide grooves 158 (FIG. 37) is guided in a rotationally-fixed manner in the housing 102. In the distal position 130 of the operating element 106, shown in FIGS. 37 to 39, the entrainment element 122, the metering member 121, the injection sleeve 120, and the metering piston 111 can thus not rotate about a longitudinal central axis 150 of the injection device 101.

The setting device 114 includes a stop element 116 which is disposed in the housing 102. The stop element 116 in the embodiment is configured so as to be sleeve-shaped and extends on the external circumference of the container 105. The stop element 116 by way of a coupling installation 126 is coupled to the axial position of the setting ring 115. The setting ring 115 is connected to the upper housing part 103 by way of a threaded connection 117. If the setting ring 115 for setting the quantity of injection liquid to be squeezed is rotated by the operator about the longitudinal central axis 150, the setting ring 115 by virtue of the threaded connection 117 thus moves in the direction along the longitudinal central axis 150. The stop element 116 is entrained by way of the coupling installation 126, and is moved in a corresponding manner in the axial direction.

The operating element 106 is mounted so as to be sprung by an activation spring 137 in the direction toward the distal position 130 of the operating element 106. In order for an injection to be released, the operating element 106 has to be moved in the proximal direction 141. A proximal end side 135 which interacts with a distal end side 136 of the upper housing part 103 and forms a stop for the proximal position 131 of the operating element 106 is provided on the operating element 106. The proximal position 131 of the operating element 106 is shown in FIGS. 40 to 42. An additional dosage of zero can be read through the viewing window 119 at the position of the setting ring 115 shown. A value of zero can also be read on the external circumference of the metering member 121 through the viewing window 107 and the opening 125 prior to the commencement of the injection. The already squeezed quantity of injection liquid herein can be read in each case through the opening 125.

The coupling 124 has been opened on account of the movement of the operating element 106 to the proximal position 131 thereof, shown in FIGS. 40 to 42. The operating element 106 has latching webs 154 which in the distal position 130 of the operating element 106 establish a rotationally-fixed connection to the entrainment element 122. The latching webs 154 in the proximal position 131 of the operating element 106 are disposed in a free space 153 of the entrainment element 122, permitting a rotation of the entrainment element 121 in relation to the operating element 106 and thus also in relation to the housing 102. The injection spring 109 acts on the injection sleeve 120 in the proximal direction. The injection sleeve 120 is guided so as to be movable in the direction along the longitudinal central axis 150 but so as to be rotationally fixed in the housing 102. The injection sleeve 120 has a proximal stop surface 147. A distal end stop 123 which interacts with the stop surface 147 and establishes the distal terminal position of the injection sleeve 120 is configured on the stop element 116. On account of the coupling of the injection sleeve 120 to the metering piston 111 by way of the metering member 121, the end stop 123 establishes the terminal position of the metering piston 111 indirectly by way of the terminal position of the injection sleeve 120. At the additional dosage of zero units, set in FIGS. 40 to 42, the stop surface 147 has a spacing d from the end stop 123. The proximal end side 142 of the setting ring 115 in this position has a spacing f from the proximal end side 140 of the upper housing part 103. As is also shown in FIG. 42, the housing parts 103 and 104 are interconnected by way of a snap-fit connection 143. The snap-fit connection 143 includes an inwardly protruding snap-fit periphery 144 of the upper housing part 103 that protrudes into a snap-fit depression 145 of the lower housing part 104. However, another connection of the two housing parts 103 and 104 can also be advantageous.

Once the coupling 124 has been opened, the injection spring 109 can move the injection sleeve 120 in the distal direction. On account thereof, the metering member 121 rotates by virtue of the threaded connection 132. However, the metering member 121 cannot move in the axial direction. The threaded connection 133, by virtue of the rotationally-fixed mounting of the metering piston 111 in the housing 102, causes a movement of the metering piston 111 in the proximal direction, this leading to injection liquid being squeezed from the container 105. The injection is terminated when the stop surface 147 bears on the end stop 123. This position is shown in FIGS. 43 to 45. The setting ring 115 has not changed its position in the squeezing of the injection liquid. The end sides 140 and 142 are also mutually spaced apart by the spacing f. The opening 125 by virtue of the movement of the injection sleeve 120 in the proximal direction has moved in relation to the metering member 121 such that the squeezed quantity of injection liquid can now be read through the opening 125. The additional set quantity of injection liquid to be squeezed of zero units can be read through the viewing window 119 in the setting ring 115.

When the operator releases the operating element 106 during the injection, the operating element 106 is pushed into the distal position 130 thereof, because the operating element 106 is pretensioned in the distal direction by the activation spring 137. The coupling 124 is closed on account thereof, and the injection is stopped. The injection procedure can be continued by pressing the operating element 106 again in the proximal direction 141.

FIGS. 46 to 48 show the injection device 101 having the maximum quantity of twenty additional units of injection liquid that can be set. In order for this quantity of injection liquid to be set, the setting ring 115 has been rotated and by virtue of the threaded connection 117 has moved in the proximal direction. The stop element 116 has been entrained in the proximal direction by virtue of the coupling installation 126. The stop surface 147 at this set dosage has a spacing e from the end stop 123, the spacing e being significantly larger than the spacing d (FIG. 42) at a lower dosage. The spacing g of the end sides 142 and 140 from the setting ring 115 and the upper housing part 103 is significantly less than the spacing f at the lower dosage (FIG. 42).

Figure 49:
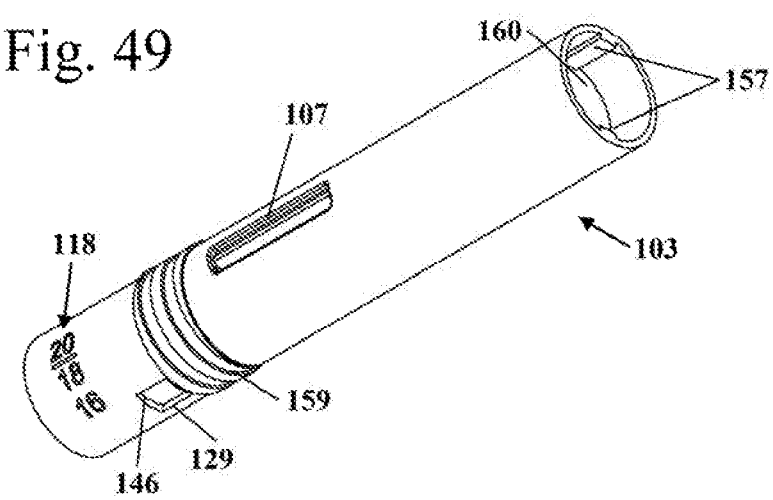
FIG. 49 shows a perspective illustration of an upper housing part of the injection device.
Figure 50:
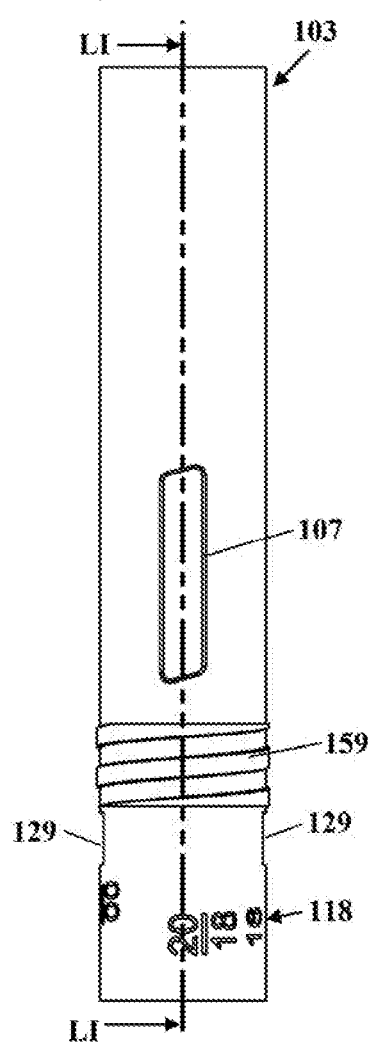
FIG. 50 shows a lateral view of the upper housing part.
Figure 51:
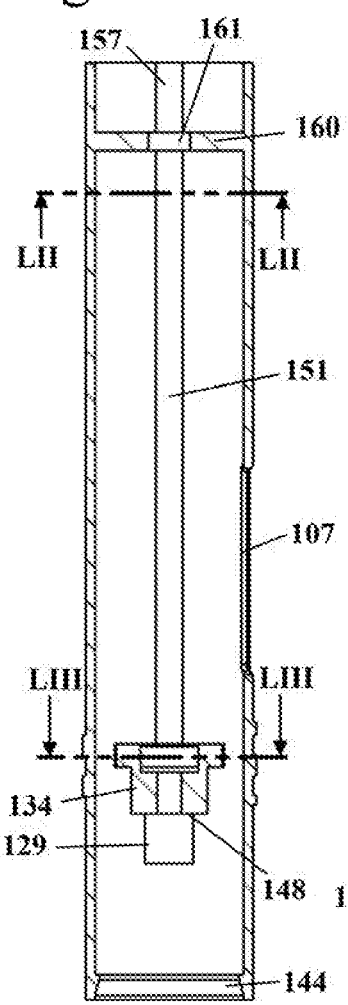
FIG. 51 shows a section along the line LI-LI in FIG. 50.
Figure 52:
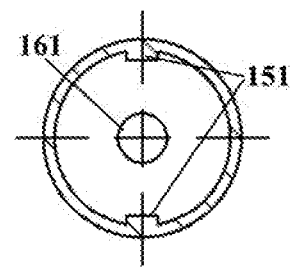
FIG. 52 shows a section along the line LII-LII in FIG. 51.
Figure 53:
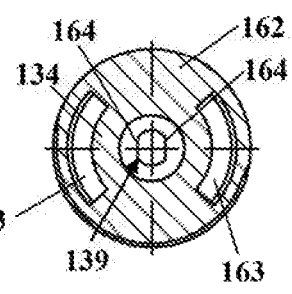
FIG. 53 shows a section along the line LIII-LIII in FIG. 51.
Figure 54:
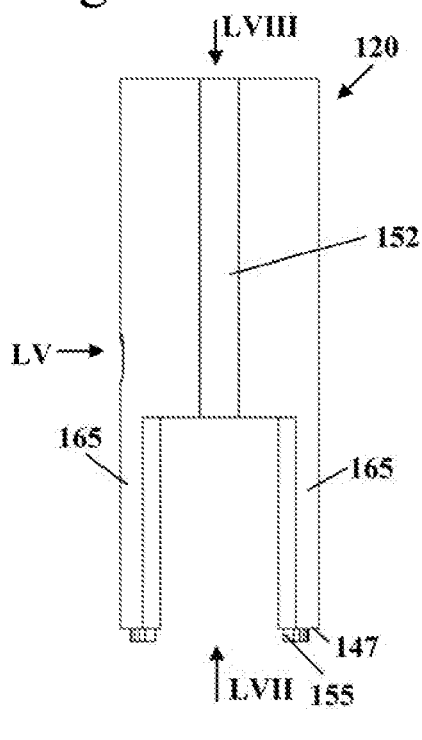
FIG. 54 shows a lateral view of an injection sleeve of the injection device.
Figure 55:
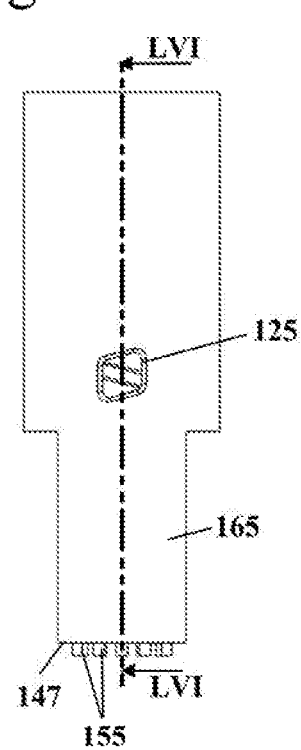
FIG. 55 shows a lateral view in the direction of the arrow LV in FIG. 54.

FIGS. 49 to 53 show the upper housing part 103 in detail. The upper housing part 103 has two openings 129 which are disposed so as to be mutually opposite and through which the coupling installation 126 (FIG. 48) can protrude from the interior of the upper housing part 103 to the setting ring 115. As is shown in FIG. 49 and FIG. 51, the openings 129 by way of the proximal end side thereof form a first, proximal stop 146 which establishes the maximum quantity of injection liquid to be squeezed, and by way of the distal end side thereof form a distal, second stop 148 which is shown in FIG. 51 and which establishes the minimum quantity of injection liquid to be squeezed. The intermediate wall 160 has a centric opening 161 through which the entrainment element 122 protrudes. The upper housing part 103 supports an external thread 159 which is part of the threaded connection 117. As is shown in FIG. 49, the upper housing part 103 on the distal side of the intermediate wall 160 has guide webs 157 which serve for the rotationally-fixed connection of the operating element 106 to the upper housing part 103. To this end, the guide webs 157 protrude into the guide grooves 158 of the operating element 106 (FIG. 37). Two guide webs 151 which are disposed so as to be mutually opposite are provided on the proximal side of the intermediate wall 160 (FIGS. 51 and 52), the guide webs 151 in the embodiment being disposed in the extension of the webs 157 and serving for the rotationally-fixed connection to the injection sleeve 120. FIGS. 51 and 53 show the configuration of the bearing portion 134 in detail. The bearing portion 134 is configured on an intermediate wall 162 which has lateral openings 163 for the injection sleeve 120, and the centric guide 139 for the piston rod 112 of the metering piston 111. The guide 139 has two flattenings 164 which are mutually opposite and serve for the rotationally-fixed mounting of the piston rod 112. On account thereof, the piston rod 112 is mounted so as to be rotationally fixed in the housing 102.

Figure 56:
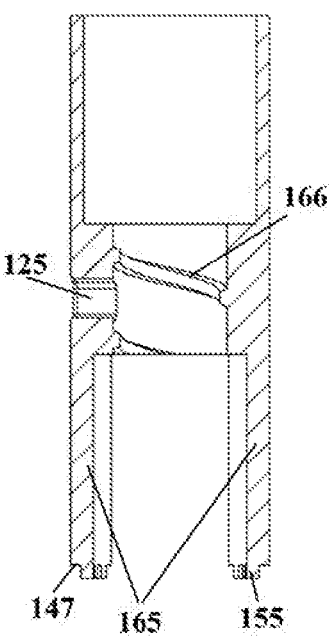
FIG. 56 shows a section along the line LVI-LVI in FIG. 55.
Figure 57:
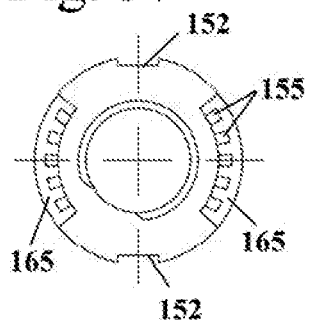
FIG. 57 shows a lateral view in the direction of the arrow LVII in FIG. 54.
Figure 59:
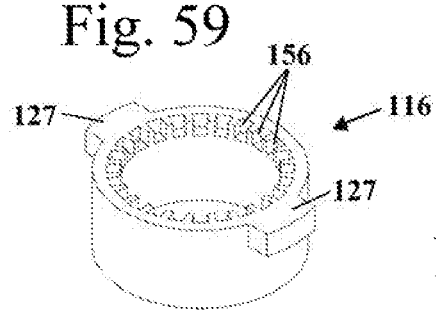
FIG. 59 shows a perspective illustration of a stop element of the injection device.
Figure 60:
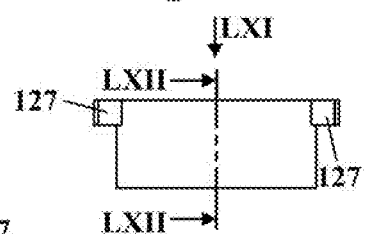
FIG. 60 shows a lateral view of the stop element.
Figure 58:
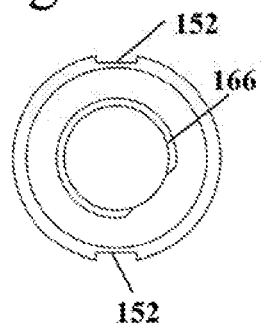
FIG. 58 shows a lateral view in the direction of the arrow LVIII in FIG. 54.
Figure 61:
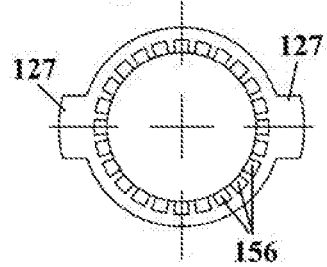
FIG. 61 shows a plan view in the direction of the arrow 61 in FIG. 60.
Figure 62:
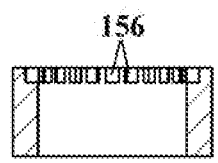
FIG. 62 shows a section along the line LXII-LXII in FIG. 60.

FIGS. 54 to 58 show the injection sleeve 120 in detail. The injection sleeve 120 on the external circumference thereof has two guide grooves 152 (FIGS. 55 and 58) into which the guide webs 151 of the upper housing part 103 protrude for the purpose of a rotationally-fixed connection. The injection sleeve 120 has two arms 165 which protrude in the proximal direction, in each case one portion of the stop surface 147 being configured on the end sides of the arms 165. A multiplicity of pins 155 which protrude into corresponding depressions 156 of the stop element 116 (FIG. 59) protrudes from the stop surface 147 in the embodiment. As is shown in FIG. 56, the injection sleeve 120 on the internal side thereof has an internal thread 166 which is part of the threaded connection 132.

The stop element 116 is shown in FIGS. 59 to 62. The stop element 116 on the distal side thereof has two mutually opposite webs 127 which protrude in a radially outward manner and which protrude through the openings 129 of the upper housing part 103 and are part of the coupling installation 126. The webs 127, conjointly with the longitudinal sides of the openings 129, simultaneously form an anti-rotation protection for the stop element 116.

Figure 63:
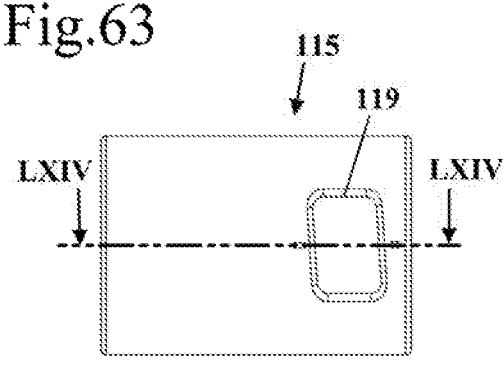
FIG. 63 shows a lateral view of a setting ring of the injection device.
Figure 64:
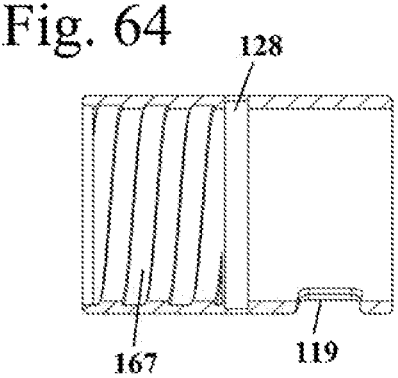
FIG. 64 shows a section along the line LXIV-LXIV in FIG. 63.
Figure 65:
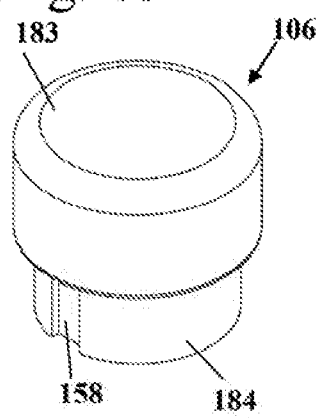
FIGS. 65 and 66 show perspective illustrations of an operating element of the injection device.
Figure 66:
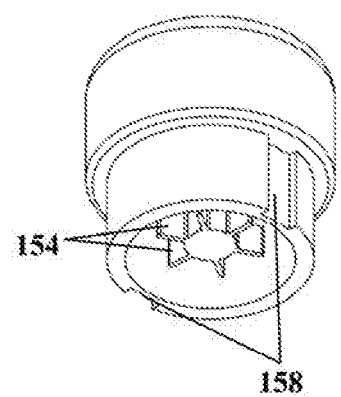
Figure 67:
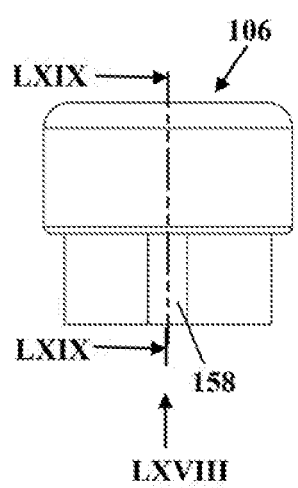
FIG. 67 shows a lateral view of the operating element.
Figure 68:
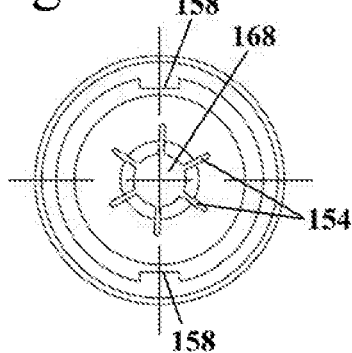
FIG. 68 shows a view of the operating element in the direction of the arrow LXVIII in FIG. 67.
Figure 69:
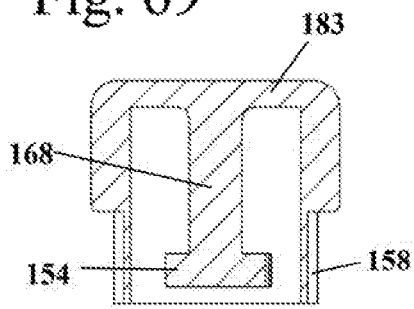
FIG. 69 shows a section along the line LXIX-LXIX in FIG. 67.
Figure 70:
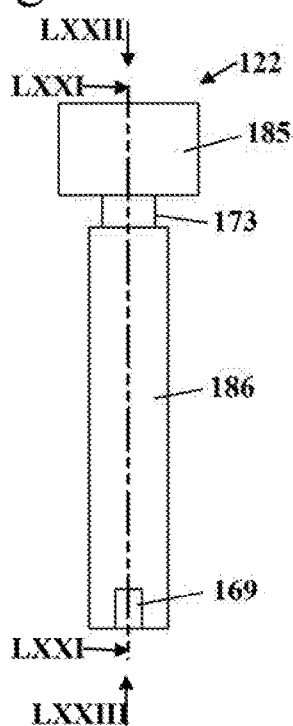
FIG. 70 shows a lateral view of an entrainment element of the injection device.
Figure 71:
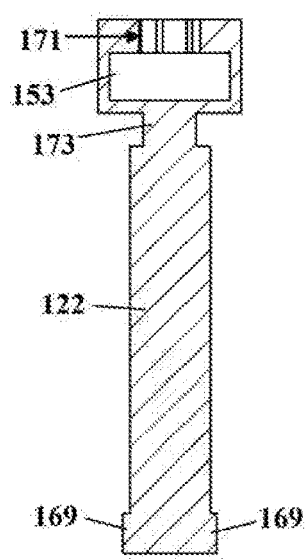
FIG. 71 shows a section along the line LXXI-LXXI in FIG. 70.

The setting ring 115 is shown in FIGS. 63 and 64. The setting ring 115 on the distal side thereof, disposed on the left in FIGS. 63 and 64, has an internal thread 167 which, conjointly with the external thread 159 of the upper housing part 103, forms the threaded connection 117. A guide 128 which is configured as an encircling groove is configured on the proximal side of the internal thread 167, webs 127 of the stop element 116 for coupling the axial position of the setting ring 115 and the stop element 116 protruding into the guide 128. A coupling that is largely free of play is advantageously provided herein, such that an exact setting of the quantity of injection liquid to be squeezed is possible.

FIGS. 65 to 69 show the operating element 106. The operating element 106 has an activation portion 183 and a sleeve portion 184, the external diameter of the latter being slightly smaller than the internal diameter of the upper housing part 103. On account thereof, the sleeve portion 184 can be pushed into the upper housing part 103. The sleeve portion 184 on the external circumference thereof supports the guide grooves 158 into which the guide webs 157 of the upper housing part 103 protrude in order for the operating element 106 to be fixed in a rotationally-fixed manner. A web 168 protrudes from the activation portion 183 in the proximal direction. The web 168 on the end thereof supports the latching webs 154 which protrude in a radially outward manner and form part of the coupling 124.

Figure 72:
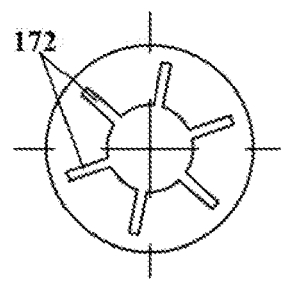
FIG. 72 shows a view of the entrainment element in the direction of the arrow LXXII in FIG. 70.
Figure 73:
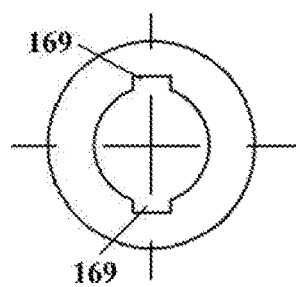
FIG. 73 shows a view of the entrainment element in the direction of the arrow LXXIII in FIG. 70.

FIGS. 70 to 73 show the entrainment element 122 in detail. The entrainment element 122 has a distal portion 185 which by way of a bearing portion 173 is separated from a proximal portion 186. The entrainment element 122 by way of the bearing portion 173 is mounted in the intermediate wall 160 of the upper housing part 103. For the assembly, the entrainment element 122 is advantageously configured in multiple parts. The distal portion 185 has a coupling portion 171 which, as is shown in FIG. 72, has a multiplicity of grooves 172. In the case of a closed coupling 124, the latching webs 154 of the operating element 106 protrude into the grooves 172 and, on account thereof, establish a rotationally-fixed connection between the operating element 106 and the entrainment element 122. The free space 153 extends on the proximal side of the coupling portion 171. The entrainment element 122 on the distal end thereof supports two connection pins 169 which are disposed so as to be mutually opposite and which serve for the rotationally-fixed connection to the metering member 121.

Figure 74:
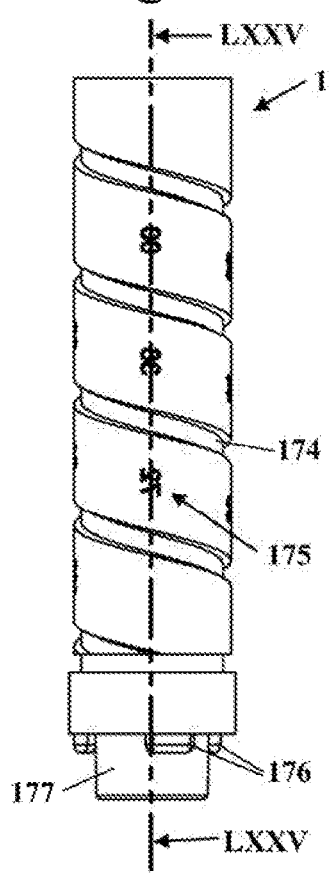
FIG. 74 shows a lateral view of a metering member of the injection device.
Figure 75:
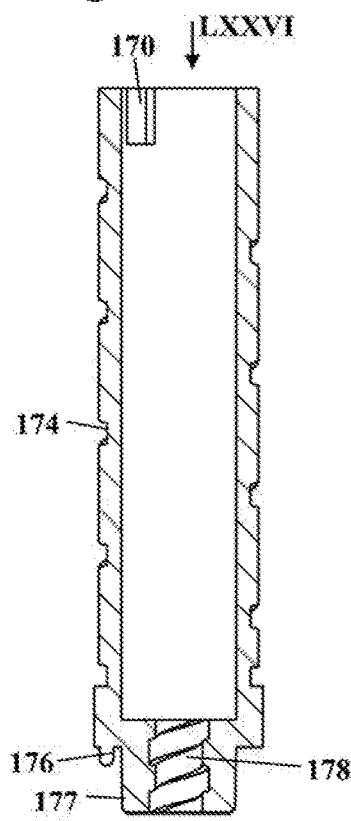
FIG. 75 shows a section along the line LXXV-LXXV in FIG. 74.
Figure 76:
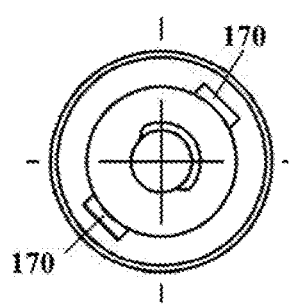
FIG. 76 shows a view of the metering member in the direction of the arrow LXXVI in FIG. 75.
Figure 77:
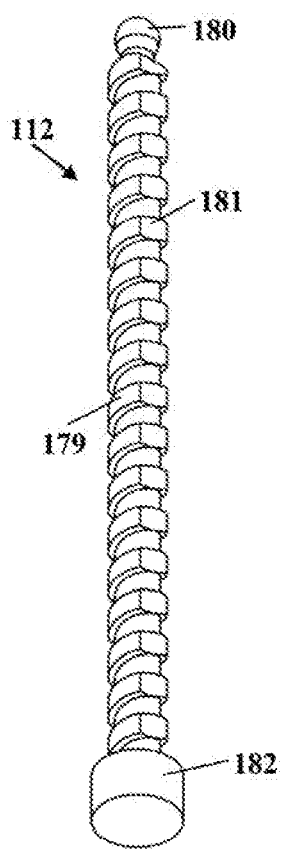
FIG. 77 shows a perspective illustration of a metering piston of the injection device.

The metering member 121 is shown in FIGS. 74 to 76. The metering member 121 is configured so as to be sleeve-shaped and on the external circumference thereof supports an external thread 174 which, conjointly with the internal thread 166 of the injection sleeve 120, forms the threaded connection 132. The metering member 121 on the external circumference thereof moreover supports a scale 175 which is visible through the opening 125 and which indicates the squeezed quantity of injection liquid. A bearing pin 177 by way of which the metering member 121 is rotatably mounted in the bearing portion 134 is disposed on the proximal side of the metering member 121. The metering member 121, adjacent to the bearing pin 177, has a plurality of protrusions 176 on which the metering member 121 bears on the bearing portion 134 and which serve for reducing friction. As is shown in FIG. 75, the metering member 121 on the distal end thereof has connection grooves 170 which are configured on the internal side which is adapted to the connection pins 169 of the entrainment element 122 and, conjointly with the latter, form the rotationally-fixed connection of the entrainment element 122 and the metering member 121. An internal thread 178 which is part of the threaded connection 133 is provided at the proximal end of the metering member 121, within the bearing pin 177.

Figure 78:
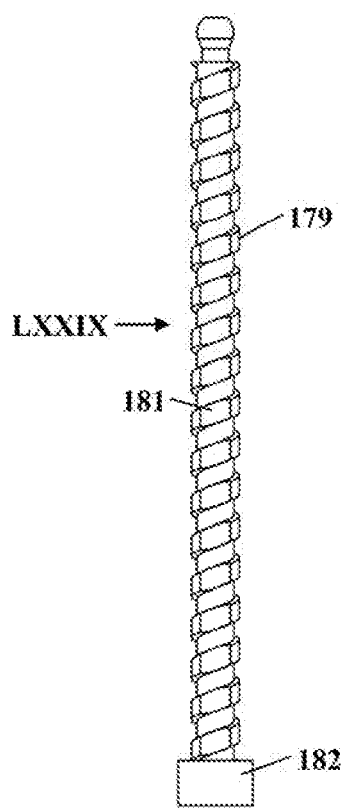
FIG. 78 shows a lateral view of the metering piston.
Figure 79:
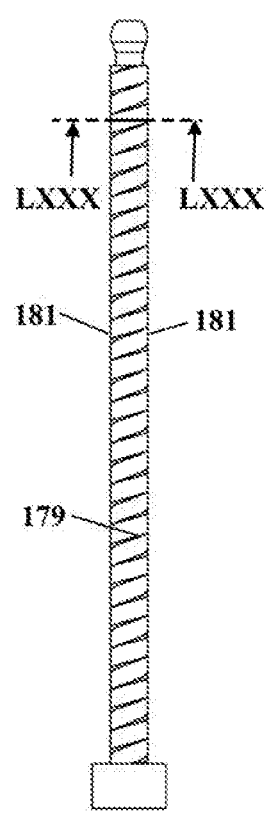
FIG. 79 shows a lateral view of the metering piston in the direction of the arrow LXXIX in FIG. 78; and, FIG. 80 shows a section along the line LXXX-LXXX in FIG. 79.
Figure 80:
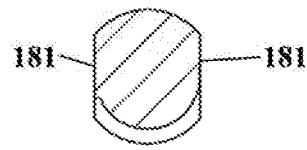

FIGS. 77 to 80 show the piston rod 112. The piston rod 112 has an external thread 179 which, conjointly with the internal thread 178, forms the threaded connection 133. The piston rod 112 on the distal side thereof, shown at the bottom in FIGS. 77 to 79, has an end disk 182 which prevents the piston rod 112 from being able to screw through the internal thread 178 of the metering member 121. The piston rod 112 on the proximal side thereof has a pin 180 for the connection to the piston disk 113. The external thread 179 has flattenings 181 which run in the longitudinal direction and which are also shown in FIGS. 78, 79, and 80. The flattenings 181 serve for the rotationally-fixed connection to the housing 102 and bear on the flattenings 164 (FIG. 53) of the upper housing part 103.

It is understood that the foregoing description is that of the preferred embodiments of the invention and that various changes and modifications may be made thereto without departing from the spirit and scope of the invention as defined in the appended claims.

What is claimed is:

1. An injection device for automatically squeezing injection liquid from a container, the injection device comprising:
   a housing;
   an injection spring configured to cause squeezing of the injection liquid from the container, the injection device defining a longitudinal central axis and a proximal direction;
   a metering piston mounted so as to be movable in a direction along the longitudinal central axis of the injection device, said metering piston being configured to, when squeezing the injection liquid, move in the proximal direction;

a setting device comprising a stop element disposed in said housing and a setting ring mounted on the housing, the setting device configured to set a quantity of the injection liquid to be squeezed, the stop element comprising an end stop which establishes a terminal position of said metering piston, and said setting device being configured to adjust a position of said end stop;

an injection sleeve mounted so as to be rotationally fixed in said housing; and a metering member mounted so as to be rotatable and axially non-displaceable in the housing, said injection sleeve being connected to said metering member via a first threaded connection, and said metering member being connected to said metering piston via a second threaded connection.

2. The injection device of claim 1, wherein said setting device is configured to adjust the position of said end stop in the direction along the longitudinal central axis of the injection device.

3. The injection device of claim 1, wherein:
said housing has a housing external side, and
said setting ring at least in part protrudes onto said housing external side and is configured to be activated by an operator.

4. The injection device of claim 3, wherein said setting ring is rotatably mounted.

5. The injection device of claim 4, wherein:
said setting ring is connected to said housing via a threaded connection, and
said setting ring is configured such that a rotation thereof causes a movement of said setting ring in the direction along the longitudinal central axis of the injection device.

6. The injection device of claim 3 further comprising a coupling installation which couples an axial position of said stop element to an axial position of said setting ring.

7. The injection device of claim 6, wherein:
said housing defines an opening therein;
said coupling installation defines a guide; and,
said coupling installation includes at least one coupling element which protrudes through said opening in said housing into said guide of said coupling installation.

8. The injection device of claim 7, wherein:
said stop element is guided so as to be rotationally fixed in said housing; and,
said at least one coupling element by way of said opening in said housing causes the rotationally-fixed guiding of said stop element.

9. The injection device of claim 6, wherein said stop element is guided so as to be rotationally fixed in said housing.

10. The injection device of claim 1, wherein said injection sleeve has a stop surface configured to interact with said end stop.

11. The injection device of claim 1, wherein:
said injection spring has a proximal spring end, and
said injection spring is supported on said injection sleeve via said proximal spring end.

12. An injection device comprising:
a housing;
a container configured to hold an injection liquid;
the injection device being configured for automatically squeezing the injection liquid from said container;
an injection spring configured to cause squeezing of the injection liquid from said container, the injection device defining a longitudinal central axis and a proximal direction;
a metering piston mounted so as to be movable in the direction along the longitudinal central axis of the injection device, said metering piston being configured to, when squeezing the injection liquid, move in the proximal direction;
a setting device comprising a stop element disposed in said housing and a setting ring mounted on the housing, the setting device configured to set a quantity of the injection liquid to be squeezed, the stop element comprising an end stop which establishes a terminal position of said metering piston, and said setting device being configured to adjust a position of said end stop;
an injection sleeve mounted so as to be rotationally fixed in said housing; and
a metering member mounted so as to be rotatable and axially non-displaceable in the housing,
said injection sleeve being connected to said metering member via a first threaded connection, and
said metering member being connected to said metering piston via a second threaded connection.

* * * * *